US010426322B2

(12) United States Patent
Tsuchiya et al.

(10) Patent No.: US 10,426,322 B2
(45) Date of Patent: Oct. 1, 2019

(54) IMAGE RECORDING APPARATUS

(71) Applicant: Olympus Corporation, Tokyo (JP)

(72) Inventors: Shusuke Tsuchiya, Tokyo (JP); Masahide Yamaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 46 days.

(21) Appl. No.: 14/333,302

(22) Filed: Jul. 16, 2014

(65) Prior Publication Data

US 2014/0375768 A1 Dec. 25, 2014

Related U.S. Application Data

(63) Continuation of application No. PCT/JP2013/084106, filed on Dec. 19, 2013.

(30) Foreign Application Priority Data

Dec. 26, 2012 (JP) .................................. 2012-283226

(51) Int. Cl.
*A61B 1/00* (2006.01)
(52) U.S. Cl.
CPC ...... *A61B 1/00163* (2013.01); *A61B 1/00011* (2013.01)
(58) Field of Classification Search
CPC .... G11B 27/34; H04N 9/7921; H04N 9/8205; H04N 5/765; H04N 9/8227; H04N 9/8063; H04N 5/232; G06F 19/321; A61B 1/0005
See application file for complete search history.

(56) References Cited

U.S. PATENT DOCUMENTS

2007/0238963 A1* 10/2007 Kaminaga .............. A61B 6/032
600/407
2008/0091065 A1* 4/2008 Oshima .................. A61B 1/045
600/109
(Continued)

FOREIGN PATENT DOCUMENTS

EP 1 779 766 A1 5/2007
EP 1 870 827 A1 12/2007
(Continued)

OTHER PUBLICATIONS

International Search Report issued in International Application No. PCT/JP2013/084106 dated Mar. 11, 2014 (with translation).

(Continued)

*Primary Examiner* — Farhan Mahmud
(74) *Attorney, Agent, or Firm* — Oliff PLC

(57) ABSTRACT

An image recording apparatus includes a first processing section that encodes an inputted medical image based on setting information and outputs a first encode result, a second processing section that encodes the inputted medical image based on the setting information and outputs a second encode result, a setting section that retains the setting information, and a control section that controls, based on the setting information corresponding to an operation signal generated based on an output signal of an electric knife, an operation signal obtained by an endoscope that generates a medical image, or an operation signal for designating a medical case scene, the first and second processing sections to output at least one of the first and second encode results and determines a recording destination of the first and second encode results based on the setting information corresponding to the operation signal.

19 Claims, 21 Drawing Sheets

(56) References Cited

U.S. PATENT DOCUMENTS

2009/0213140 A1* 8/2009 Ito .................. A61B 1/00006
                                                    345/629
2010/0274082 A1  10/2010 Iguchi et al.

FOREIGN PATENT DOCUMENTS

| EP | 2 085 904 A2 | 8/2009 |
|----|---|---|
| EP | 2 245 978 A1 | 11/2010 |
| EP | 2 687 146 A1 | 1/2014 |
| JP | A-8-107878 | 4/1996 |
| JP | A-2003-24273 | 1/2003 |
| JP | A-2004-344390 | 12/2004 |
| JP | 2006-271870 A | 10/2006 |
| JP | A-2006-271871 | 10/2006 |
| JP | 2007-007339 A | 1/2007 |
| JP | A-2007-319342 | 12/2007 |
| JP | A-2008-282 | 1/2008 |
| JP | A-2008-86665 | 4/2008 |
| JP | A-2009-207610 | 9/2009 |
| JP | A-2010-253156 | 11/2010 |
| JP | 2012-217632 A | 11/2012 |
| WO | WO 2012/005108 A1 | 1/2012 |
| WO | 2012/165381 A1 | 12/2012 |

OTHER PUBLICATIONS

Feb. 9, 2016 Extended European Search Report issued in EP 13869363.5.

Aug. 26, 2014 Office Action issued in Japanese Patent Application No. 2014-531018.

* cited by examiner

IMAGE RECORDING APPARATUS

CROSS REFERENCE TO RELATED APPLICATION

This application is a continuation application of PCT/JP2013/084106 filed on Dec. 19, 2013 and claims benefit of Japanese Application No. 2012-283226 filed in Japan on Dec. 26, 2012, the entire contents of which are incorporated herein by this reference.

BACKGROUND OF THE INVENTION

1. Field of the Invention

The present invention relates to an image recording apparatus that records an image obtained by a medical apparatus such as an endoscope.

2. Description of the Related Art

Conventionally, an endoscope is widely adopted in a medical field and the like. In recent years, improvement of image quality (high vision) of the endoscope has advanced, tissues in an abdominal cavity such as a peritoneum structure and a blood stream can be clearly visually recognized, and an endoscopic operation can be more safely and surely performed.

In a medical institution, a large number of modalities such as an endoscope, an X-ray, and an ultrasound diagnostic apparatus are sometimes combined to record various medical images such as an endoscopic image, an ultrasound image, and an X-ray image. In a conventional recording apparatus that records the medical images, data after the recording can be outputted in various forms according to uses. For example, during an operation, the medical images can be recorded in a semiconductor recording device such as a USB memory or an optical medium in a computer-editable format on a real-time basis. The medical images can also be recorded in the optical medium in a format reproducible by a general-purpose video player. Further, the medical images can be transferred to a server through a network and recorded to share data.

Incidentally, it is conceivable to use the medical images as medical images for backup such as evidence images for the purpose of recording a medical case and use the medical images as an educational material. For example, concerning an important dissection scene in the medical case, recorded images can be shared in a scientific society and an in-hospital conference and utilized for education of young doctors.

When the medical images are recorded as the medical images for backup, since it is necessary to record the entire medical case for a long time, recording at relatively low image quality is performed taking into account a recording capacity. On the other hand, when the medical case is recorded as the educational material, since the recorded images make it easy to observe the medical case, it is desirable to record the medical images at highest image quality as much as possible.

Therefore, in a conventional image recording apparatus, medical images can be recorded with an image size, a compression ratio, a format, and the like designated during recording of a medical case according to a purpose (see, Japanese Patent Application Laid-Open Publication No. 2008-86665).

SUMMARY OF THE INVENTION

An image recording apparatus according to the present invention includes: a first processing section that encodes an inputted medical image on the basis of setting information and outputs a first encode result; a second processing section that encodes the inputted medical image on the basis of the setting information and outputs a second encode result; a setting section that retains the setting information; and a control section that controls, on the basis of the setting information corresponding to an operation signal generated on the basis of an output signal of an electric knife, an operation signal obtained by an endoscope that generates a medical image, or an operation signal for designating a medical case scene, the first and second processing sections to output at least one of the first and second encode results and determines a recording destination of the first and second encode results on the basis of the setting information corresponding to the operation signal.

DETAILED DESCRIPTION OF THE PREFERRED EMBODIMENTS

Embodiments of the present invention are explained in detail below with reference to the drawings.

(First Embodiment)

Figure 1:
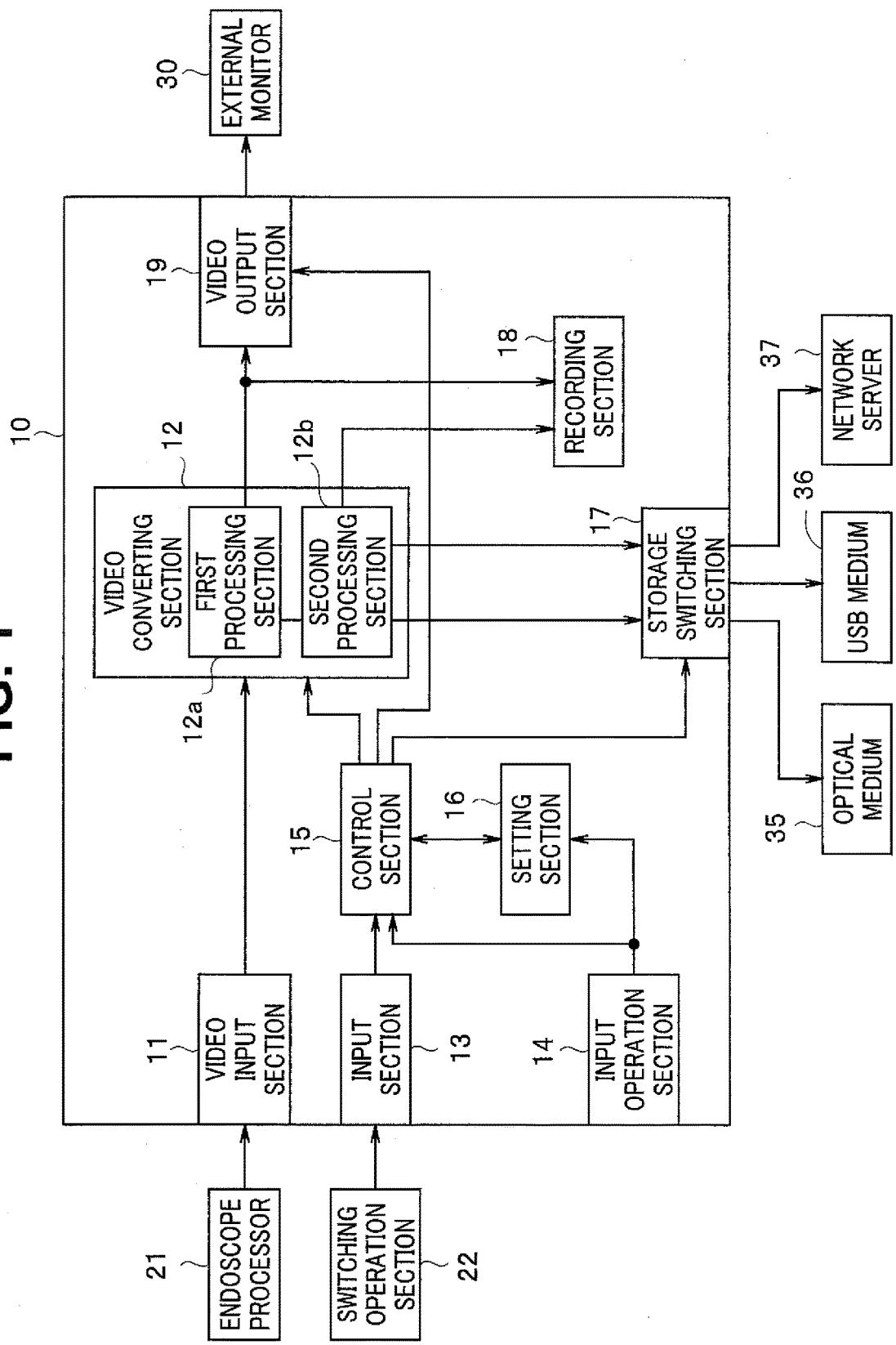
FIG. 1 is a block diagram showing an image recording apparatus according to a first embodiment of the present invention.

FIG. 1 is a block diagram showing an image recording apparatus according to a first embodiment of the present invention.

In the present embodiment, an example is explained in which an endoscope processor 21 is used as a device that outputs medical information. The endoscope processor 21 can capture an image from a not-shown endoscope or the like, perform image signal processing, and generate a medical image such as an endoscopic image. The medical image from the endoscope processor 21 is supplied to an image recording apparatus 10. The endoscope processor 21 can output the endoscopic image as a high-definition image.

A switching operation section 22 is configured by an operation section, which a surgeon can relatively easily operate during an operation, for example, a button and various scope switches, which are provided in the not-shown endoscope, or a not-shown foot switch. The switching operation section 22 can output a switching signal based on user operation to the image recording apparatus 10.

The medical image from the endoscope processor 21 is inputted to a video input section 11 of the image recording apparatus 10. The video input section 11 is an interface suitable for image transmission and captures the medical image from the endoscope processor 21. Note that, as the video input section 11, various terminals such as a DVI (digital visual interface) terminal, an SDI (serial digital interface) terminal, an RGB terminal, a Y/C terminal, and a VIDEO terminal can be adopted. The video input section 11 can capture not only the medical image of the endoscope processor 21 but also various medical images of, for example, an ultrasound device, an operating field camera, an X-ray observation device, and an endoscope processor different from the endoscope processor 21.

The switching signal from the switching operation section 22 is inputted to an input section 13. For example, as the input section 13, an interface based on an RS-232C standard can be adopted. The input section 13 outputs the switching signal from the switching operation section 22 to a control section 15.

The medical image from the video input section 11 is given to a video converting section 12. The video converting section 12 includes first and second processing sections 12a and 12b that encode the medical image into video signals of a predetermined image format. For example, the first and second processing sections 12a and 12b are capable of converting the inputted medical image into video signals of an MPEG2 format, an MPEG-4AVC/H.264 format, or the like.

The first and second processing sections 12a and 12b of the video converting section 12 can give the video signals after the encoding to a recording section 18 and cause the recording section 18 to record the video signals. As the recording section 18, for example, a built-in HDD (hard disk device) can be adopted. The recording section 18 records the inputted video signals. The recording section 18 is configured to be capable of not only recording a video signal of one system but also recording video signals of two systems.

The first and second processing sections 12a and 12b of the video converting section 12 respectively output the video signals after the encoding to a storage switching section 17 in order to cause an external medium to record the video signals. The storage switching section 17 is controlled by the control section 15 and can record video signals inputted to various recording media on the outside.

For example, the storage switching section 17 includes an optical drive device that performs recording in and reproduction from an optical medium 35 such as a Blu-ray disk and a USB recording and reproducing section that performs recording in and reproduction from a USB medium 36 such as a USB memory (not shown in the figure). Further, the storage switching section 17 includes a network interface or the like that transfers the video signals to a network server 37 and causes the network server 37 to record and reproduce the video signals (not shown in the figure). Note that the recording section 18 is controlled by the control section 15 (not shown in the figure) and configured to perform recording in association with encode processing of the medical image by the video converting section 12. The recording section 18 records the video signals encoded by the video converting section 12.

The video signal from the first processing section 12a of the video converting section 12 is supplied to a video output section 19. After decoding the video signal from the first processing section 12a, the video output section 19 can give the video signal to an external monitor 30 and cause the external monitor 30 to display the medical image. Note that the video converting section 12 may output the inputted video signals to the video output section 19 without encoding the video signal. In this case, the video output section 19 directly gives the video signals from the video converting section 12 to the external monitor 30 and causes the external monitor 30 to display the medical image.

In the present embodiment, the encode processing of the first and second processing sections 12a and 12b of the video converting section 12 is controlled by the control section 15. A switching signal from the input section 13 and an operation signal from an input operation section 14 are given to the control section 15. The input operation section 14 generates an operation signal based on user operation on an operation key, an operation button, or the like not shown in the figure and outputs the operation signal to the control section 15 and a setting section 16. Various kinds of setting for the encode processing of the first and second processing sections 12a and 12b of the video converting section 12 can be set in the setting section 16 according to the user operation on the input operation section 14. The setting section 16 stores setting information based on operation of the input operation section 14 in a not-shown memory.

The control section 15 reads out the setting information of the setting section 16 on the basis of the operation signal and the switching signal and controls the encode processing of the first and second processing sections 12a and 12b and the storage switching section 17 on the basis of the setting information. For example, the setting information includes information such as resolution, a compression form, and a compression ratio in the encode processing and information concerning a storage destination (a simultaneous storage destination).

Note that, when the medical image is inputted via the video input section 11, the control section 15 may control the video converting section 12 to automatically start encode of the inputted medical image. The control section 15 may start the encode of the inputted medical image according to operation of the input operation section 14. The control section 15 may capture, via a not-shown interface, for example, control information generated in response to operation of a recording start button or a recording end button provided in the not-shown endoscope or the endoscope processor 21 and perform a start and an end of the encode of the medical image on the basis of the control information.

In the present embodiment, by using the setting information of the setting section 16, for example, the control section 15 can control the first processing section 12a to subject the inputted medical image to the encode processing at a high compression ratio and control the second processing section 12b to subject the inputted medical image to the encode processing at a low compression ratio. Consequently, a video signal obtained by the first processing section 12a is a video signal having a low bit rate and relatively low image quality. A video signal obtained by the second processing section 12b is a video signal having a high bit rate and relatively high image quality.

Other than causing the first processing section 12a and the second processing section 12b to change a compression rate to perform the encode, the control section 15 may cause the first processing section 12a and the second processing section 12b to change an image size and a format to perform the encode or may change the compression ratio and the image size and the format in combination. For example, the control section 15 may cause the first processing section 12a to output a video signal of an image size of HD or SD and cause the second processing section 12b to output a video signal of an image size of full HD. For example, this is extremely useful when a medical case is observed on a large-screen monitor in a meeting room or the like by recording the video signal of the image size of the full HD as an image for education. On the other hand, as an image for backup, a small monitor only has to be able to be used to display the image. The image is recorded by the video signal of the image size of the SD. When formats adapted to reproducing apparatuses for the images for backup and for education are different, formats during encoding in the first and second processing sections 12a and 12b only have to be determined according to the formats adapted to the reproducing apparatuses.

Note that, for convenience of explanation, only the image quality is explained below. However, various kinds of setting are also possible concerning the image size and the format on the basis of the setting information. In the following explanation, concerning outputs of the first and second processing sections 12a and 12b, low image quality and high image quality mean relative image quality and mean that the video signal from the second processing section 12b is higher in image quality than the video signal from the first processing section 12a.

In the present embodiment, in an initial state, the control section 15 causes only the first processing section 12a to operate. Every time the switching signal from the switching operation section 22 is generated, the control section 15 switches a start and an end of the operation of the second processing section 12b. Consequently, for example, over an entire period of a medical case, the video signal from the first processing section 12a is supplied to the storage switching section 17, the recording section 18, and the video output section 19. The low image quality video signal is recorded over the entire period of the medical case.

When the operation of the second processing section 12b is started by the switching signal, for example, the high image quality video signal from the second processing section 12b is given to the storage switching section 17 and the recording section 18 and recorded. When the operation of the second processing section 12b is turned off by the switching signal, the storage switching section 17 and the recording section 18 make a file of and record the high image quality video signal from the second processing section 12b.

The control section 15 can control the video output section 19 to display various menu screens and the like on a display screen of the external monitor 30. The control section 15 is configured to be capable of easily performing recording setting by the input operation section 14 by GUI (graphical user interface)-displaying, for example, setting processing for the setting information of the setting section 16 on the external monitor 30 and a not-shown touch panel mounted on the recording device.

FIG. 2 to FIG. 5 are explanatory diagrams showing menu displays of the recording setting.

Figure 2:
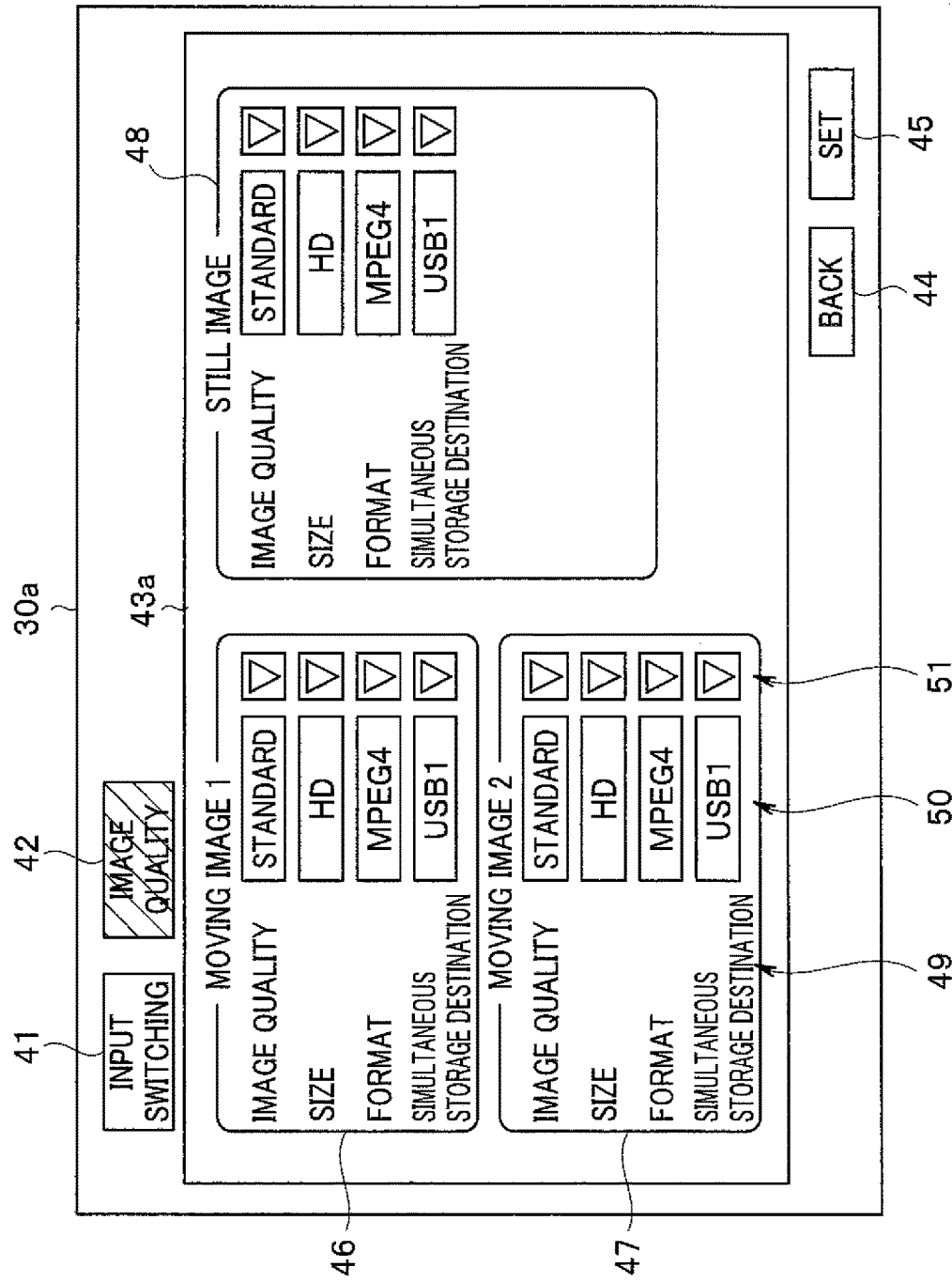
FIG. 2 is an explanatory diagram showing a menu display for recording setting.
Figure 3:
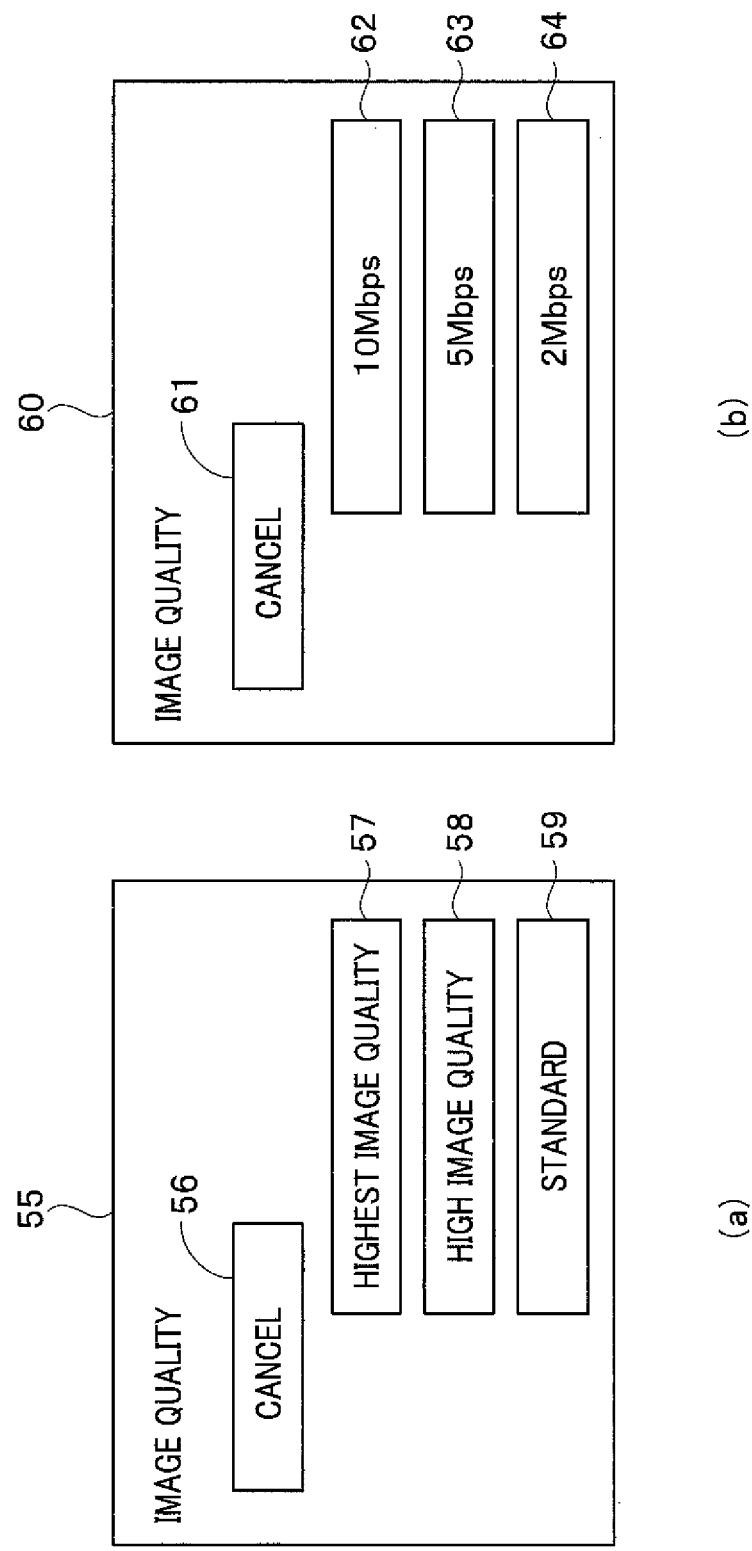
FIG. 3 is an explanatory diagram showing a menu display for the recording setting.
Figure 4:
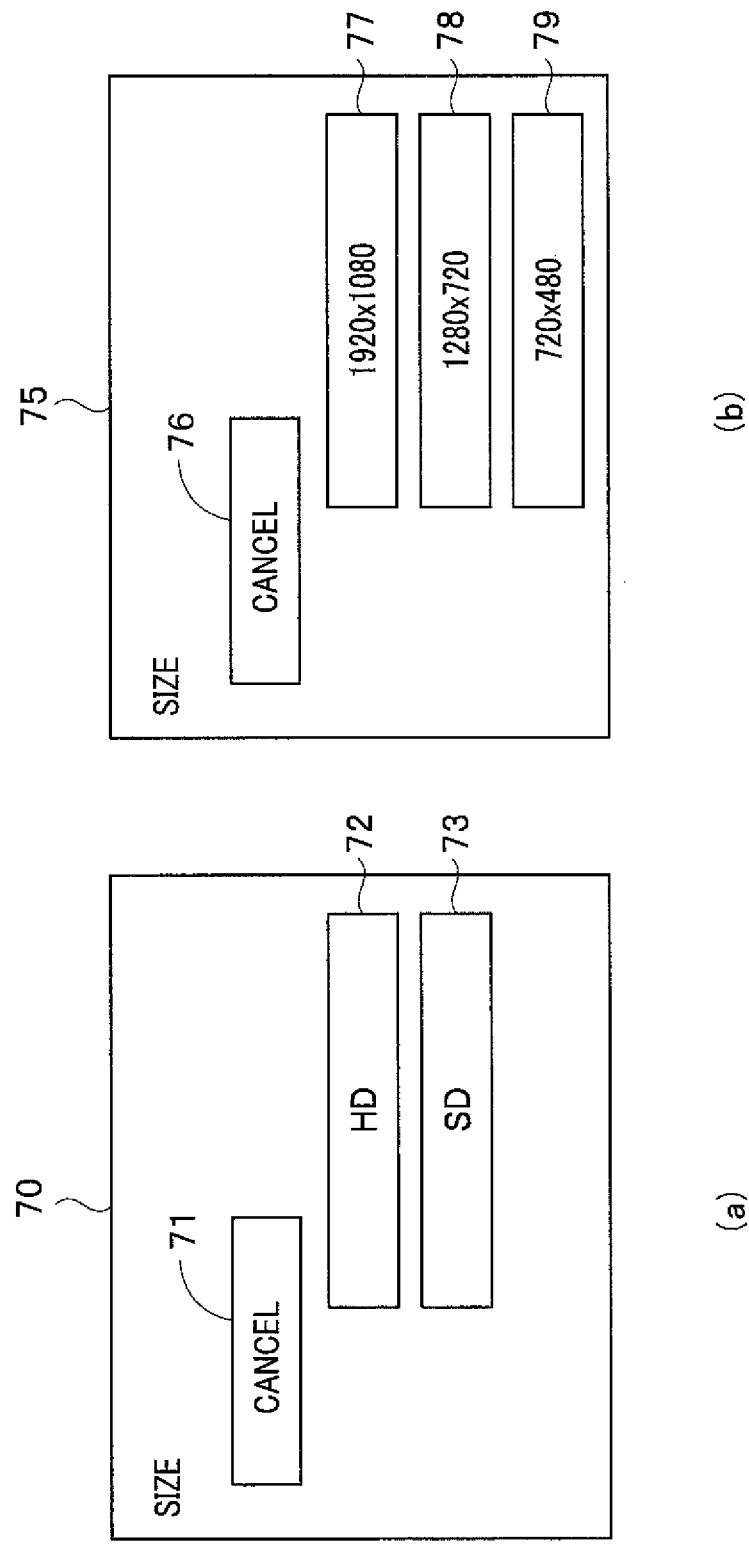
FIG. 4 is an explanatory diagram showing a menu display for the recording setting.
Figure 5:
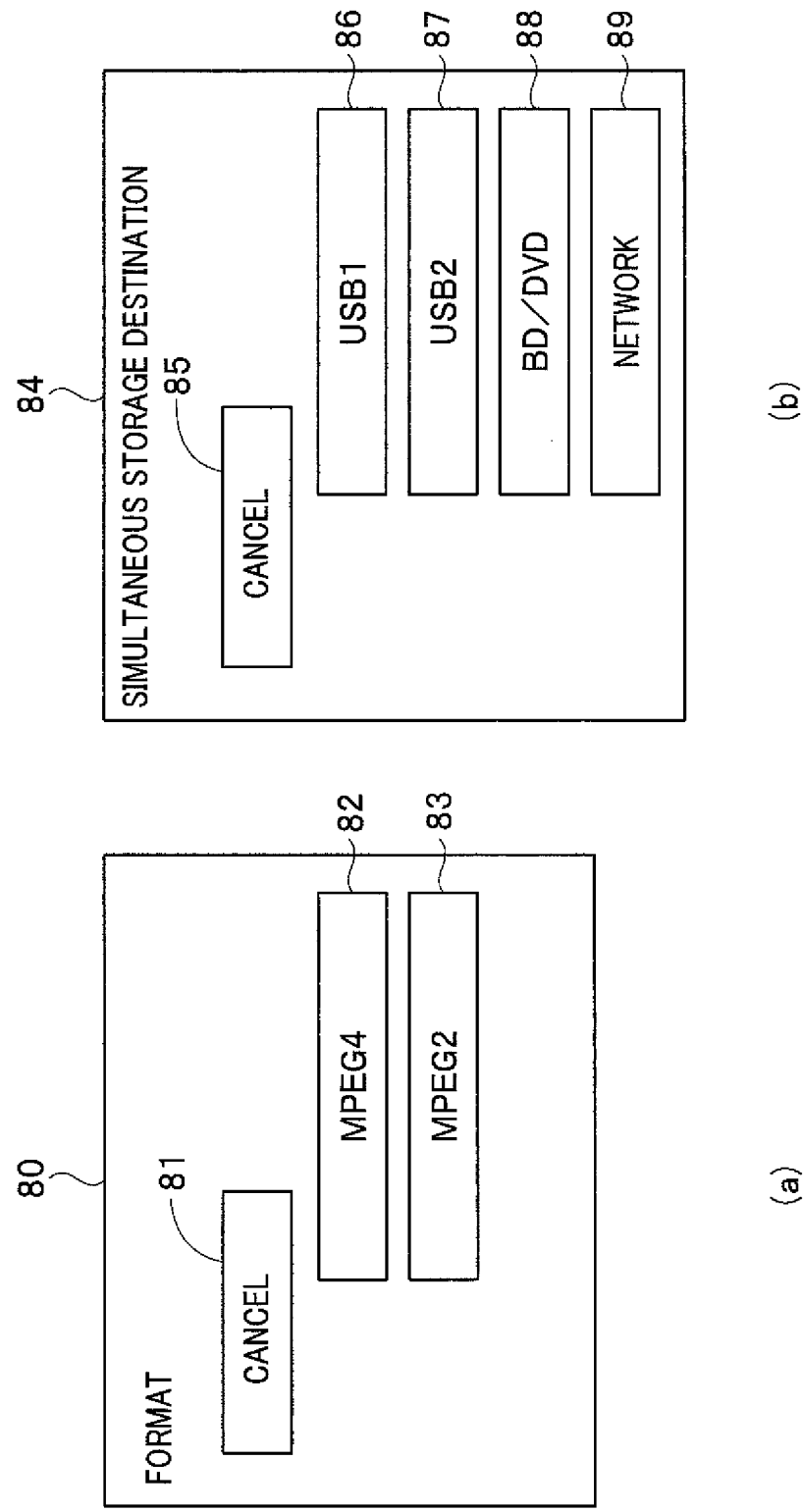
FIG. 5 is an explanatory diagram showing a menu display for the recording setting.

FIG. 2 shows a menu display for the recording setting displayed on a display screen 30a of the external monitor 30. In the menu display, an input switching button 41, an image quality button 42, a back button 44, a setting button 45, and a setting area 43a are displayed. FIG. 2 shows an example in which the setting area 43a concerning image quality is displayed by operation of the image quality button 42.

In the setting area 43a, a setting area (moving image 1) 46 concerning recording setting for a moving image of the first processing section 12a, a setting area (moving image 2) 47 concerning recording setting for a moving image of the second processing section 12b, and a setting area (still image) 48 concerning recording setting for a still image of the second processing section 12b are displayed.

In the respective setting areas 46 to 48, an item display 49 is displayed in a left field, a present setting value 50 is displayed in a center field, and a setting change button 51 is displayed in a right field. As shown in the item display 49 of the setting areas 46 to 48, as items that can be set, there are image quality, a size, a format, and a simultaneous storage destination. As present setting values, concerning the moving image 1 of the setting area 46, standard is set as the image quality, HD is set as the size, MPEG4 is set as the format, and USB1 is set as the simultaneous storage destination.

When the setting change button 51 of an item of the image quality is operated, a display shown in FIG. 3(a) or 3(b) is displayed. FIG. 3(a) shows an example of a menu display 55 for a setting change of the image quality. As shown in FIG. 3(a), in the menu display 55, a cancel button 56, a highest image quality button 57, a high image quality button 58, and a standard button 59 are displayed. When the cancel button 56 is operated, display of the menu display 55 is extinguished. When the highest image quality button 57, the high image quality button 58, and the standard button 59 are respectively operated, highest image quality, high image quality, and standard image quality are respectively set as image quality.

An example of the other menu display for the setting change of the image quality is shown in FIG. 3(b). As shown in FIG. 3(b), in a menu display 60, a cancel button 61, a 10 Mbps button 62, a 5 Mbps button 63, and a 2 Mbps button 64 are displayed. When the cancel button 61 is operated, display of the menu display 60 is extinguished. When the 10 Mbps button 62, the 5 Mbps button 63, and the 2 Mbps button 64 are respectively operated, 10 Mbps, 5 Mbps, and 2 Mbps are respectively set as image quality.

When the setting change button 51 of an item of the size shown in FIG. 2 is operated, a display shown in FIG. 4(a) or 4(b) is displayed. FIG. 4(a) shows an example of a menu display 70 for a setting change of the size. As shown in FIG. 4(a), on the menu display 70, a cancel button 71, an HD button 72, an SD button 73 are displayed. When the cancel button 71 is operated, display of the menu display 70 is extinguished. When the HD button 72 and the SD button 73 are respectively operated, HD and SD are respectively set as sizes.

FIG. 4(b) shows an example of another menu display for the setting change of the size. As shown in FIG. 4(b), in a menu display 75, a cancel button 76, a full HD button 77, an HD button 78, and an SD button 79 are displayed. When the cancel button 76 is operated, display of the menu display 75 is extinguished. When the full HD button 77, the HD button 78, and the SD button 79 are respectively operated, 1920× 1080, 1280×720, and 720×480 are respectively set as image sizes.

When the setting change buttons 51 of items of the format and the simultaneous storage destination shown in FIG. 2 are respectively operated, a display shown in FIG. 5(a) or 5(b) is displayed. FIG. 5(a) shows an example of a menu display 80 for the setting change of the format. FIG. 5(b) shows an example of a menu display 84 for the setting change of the simultaneous storage destination.

As shown in FIG. 5(a), in the menu display 80, a cancel button 81, an MPEG4 button 82, and an MPEG2 button 83 are displayed. When the cancel button 81 is operated, display of the menu display 80 is extinguished. When the MPEG4 button 82 and the MPEG2 button 83 are respectively operated, MPEG-4AVC/H.264 and MPEG2 are respectively set as encoding formats.

FIG. 5(b) shows a menu display 84 for the setting change of the simultaneous storage destination. As shown in FIG. 5(b), in the menu display 84, a cancel button 85, a USB1 button 86, a USB2 button 87, a BD/DVD button 88, and a network button 89 are displayed. FIG. 5(b) shows an example in which the storage switching section 17 has two systems as a USB recording and reproducing section and an optical drive device is capable of performing recording and reproduction on both media of Blu-ray and DVD. When the cancel button 85 is operated, display of the menu display 84 is extinguished. When the USB1 button 86, the USB2 button 87, and the BD/DVD button 88, and the network button 89 are respectively operated, USB1, USB2, BD/DVD, and network are respectively set as simultaneous storage destinations.

The setting information can be registered in the setting section 16 by operation of the input operation section 14 or the like with respect to the menu displays shown in FIG. 2 to FIG. 5. In the present embodiment, as explained above, the control section 15 reads out the setting information of the setting section 16 and controls the first and second processing sections 12a and 12b and the storage switching section 17. In this way, processing contents of the encode processing in the first and second processing sections 12a and 12b and the simultaneous storage destination of the video signals after the encoding are determined according to the setting information.

Next, an operation in the present embodiment configured as explained above is explained with reference to a flowchart of FIG. 6.

First, an operator performs setting for recording in the setting section 16 via the input operation section 14. The setting section 16 causes a not-shown memory to store setting information corresponding to the recording setting. Thereafter, recording of a medical case or the like is performed on the basis of the setting information set in the setting section 16. For example, in the encode processing by the first processing section 12a, encoding processing to an image at a relatively low bit rate, for example, an image of SD image quality is designated by the setting information. On the other hand, in the encode processing by the second processing section 12b, encoding processing to an image at a relatively high bit rate, for example, an image of full HD image quality is designated by the setting information.

Figure 6:
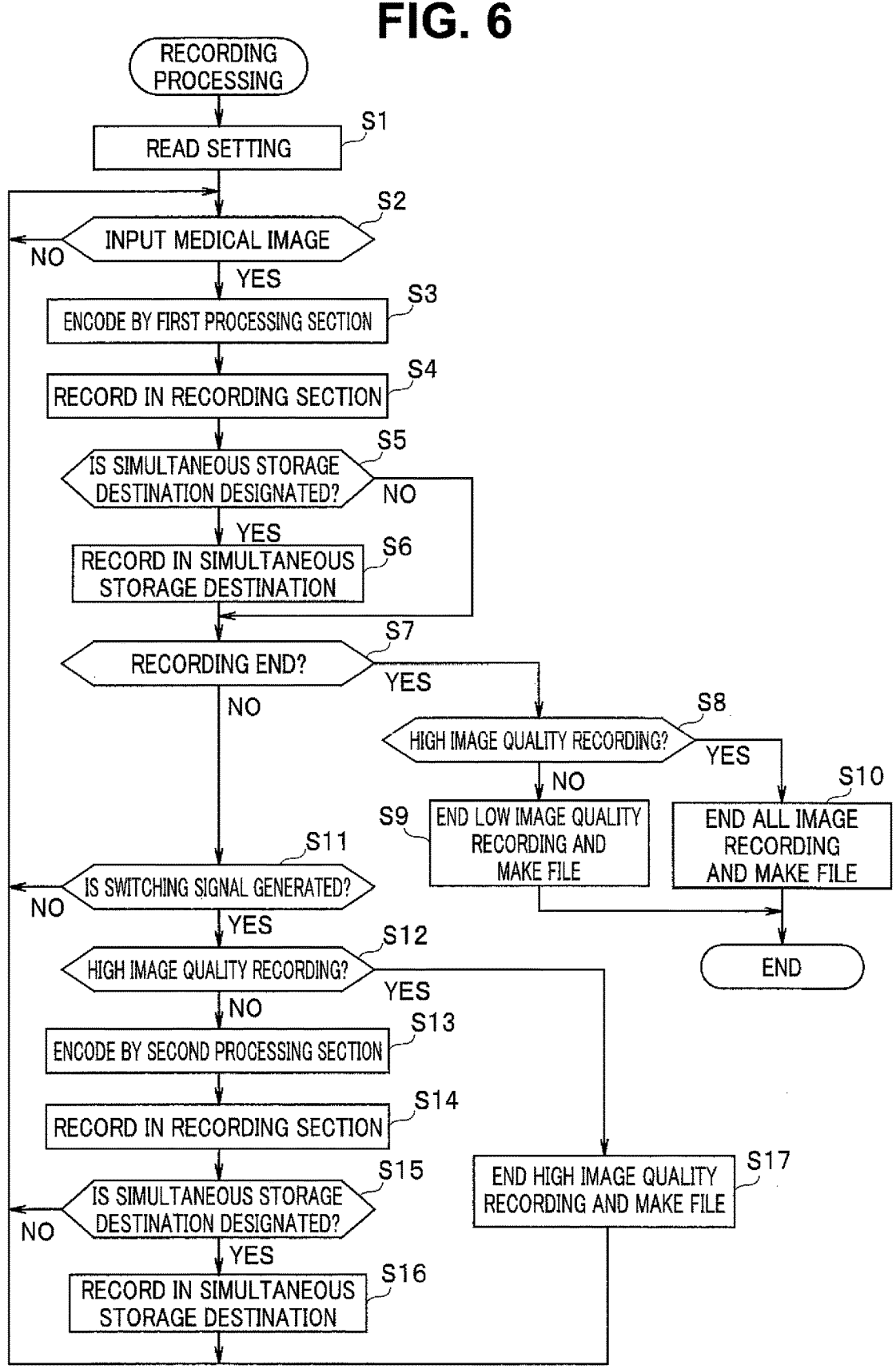
FIG. 6 is a flowchart for explaining an operation in the first embodiment.

The control section 15 reads the setting information in step S1 in FIG. 6. When a medical image is inputted via the video input section 11 (step S2), the control section 15 causes the first processing section 12a to start an operation. The first processing section 12a starts encode of the medical image (step S3). Video signals obtained by being encoded are sequentially supplied to the recording section 18 and recording is started (step S4).

When a simultaneous storage destination is designated by the setting information, that is, when setting for recording an image from the first processing section 12a in an external medium and a network server is performed (step S5), recording in the simultaneous storage destination is started according to the setting (step S6).

In step S7, the control section 15 determines whether a recording end concerning the medical case is instructed. When the recording end is instructed, in step S8, the control section 15 determines whether recording in high image quality recording is performed. When the high image quality recording is not performed, that is, when the encode processing and recording processing of the image after the encode by the second processing section 12b are not performed, in step S9, the control section 15 causes the first processing section 12a to end the encode processing and the low image quality recording by the first processing section 12a, makes a file, and ends the recording processing.

In this way, the encode processing and the recording processing by the first processing section 12a continue until recording end operation for one medical case is performed. At least one recording data by a low image quality image is generated for one medical case.

When determining in step S7 that the recording end operation is not performed, subsequently, the control section 15 determines whether a switching signal is generated (step S11). When the switching signal is not generated, the control section 15 returns the processing to step S3 and continues the encode processing.

It is assumed that, for example, an important scene for education now appears. In order to record the important scene, the surgeon operates the switching operation section 22 configured by, for example, the scope switches of the endoscope. Consequently, a switching signal is generated from the switching operation section 22. The switching signal is inputted to the control section 15 via the input section 13. When the switching signal is inputted, if the high image quality recording is not already being performed (step S12), the control section 15 starts an operation of the second processing section 12b on the basis of the setting information from the setting section 16 (step S13).

The second processing section 12b encodes the inputted medical image to be a high-definition image of, for example, the full HD image quality. Video signals after the encode are supplied to the recording section 18 and sequentially recorded. That is, the recording section 18 simultaneously records a low image quality image from the first processing section 12a and a high image quality image from the second processing section 12b.

When a simultaneous storage destination is designated by the setting information, that is, when setting for recording an image from the second processing section 12b in the external medium and the network server is performed (step S15), recording in the simultaneous storage destination is started according to the setting (step S16).

It is assumed that the important scene ends here and the surgeon stops the recording for education. In this case, the surgeon operates the switching operation section 22 configured by, for example, the scope switches of the endoscope. Consequently, a switching signal is generated from the switching operation section 22 and inputted to the control section 15 via the input section 13. When the switching signal is inputted, in step S12, the control section 15 determines whether high image quality recording is already being performed. When the high image quality recording is being performed, that is, when the encode processing and the recording processing for an image after the encode by the second processing section 12b are performed, in step S17, the control section 15 causes the second processing section 12b to end the encode processing and the high image quality recording by the second processing section 12b, makes a file, and ends the recording processing by the high image quality.

Thereafter, the processing in steps S3 to S17 is repeated until end operation for medical case recording is performed. In this way, recording data by the high image quality recording is made into a file and recorded in every operation of the switching operation section 22 of the surgeon.

Note that, when the high image quality recording is performed at the end of the recording, after the determination in steps S7 and S8, the processing shifts to step S10. The control section 15 ends the encode processing by the first and second processing sections 12a and 12b and the low image quality and high image quality recording processing by the recording section 18 and the storage switching section 17, makes a file, and ends the recording processing.

In this way, in the present embodiment, for example, over an entire period of a medical case, recording at relatively low image quality for backup and the like is performed by the first processing section. In a period designated by a surgeon, recording at relatively high image quality for education and the like is performed by the second processing section. Consequently, it is possible to easily record images of the two kinds of image quality for backup and for education. The high image quality image for education is generated only in the period designated by the surgeon. Therefore, complicated work for, for example, extracting a relevant portion out of a long time after an operation is unnecessary. In the recording of the high image quality image for education, it is unnecessary to stop the recording of the image for backup. It is possible to generate only one file for backup for one medical case. It is possible to start and end the recording of the high image quality image according to simple operation by the surgeon. Complicated work such as a stop, a start, and setting operation of recording is unnecessary. It is possible to remarkably improve operability. Further, it is possible to designate a recording destination on the basis of the setting information. It is possible to store a low image quality video signal and a high image quality video signal in an appropriate storage destination. Consequently, even when a usable medium is determined for each use, recording in a corresponding medium can be automatically performed. This is excellent in convenience. In this way, recording corresponding to a use can be performed in a medical case. Labor for a setting change, labor for searching for a desired image, labor for converting image quality after an operation, and the like are reduced to make it easy to utilize recording data.

Note that, in the embodiment, an example is explained in which video signals by the first processing section are continuously recorded in a medical case. However, control may be performed to record one of video signals by the first processing section and video signals by the second processing section.

(Second Embodiment)

Figure 7:
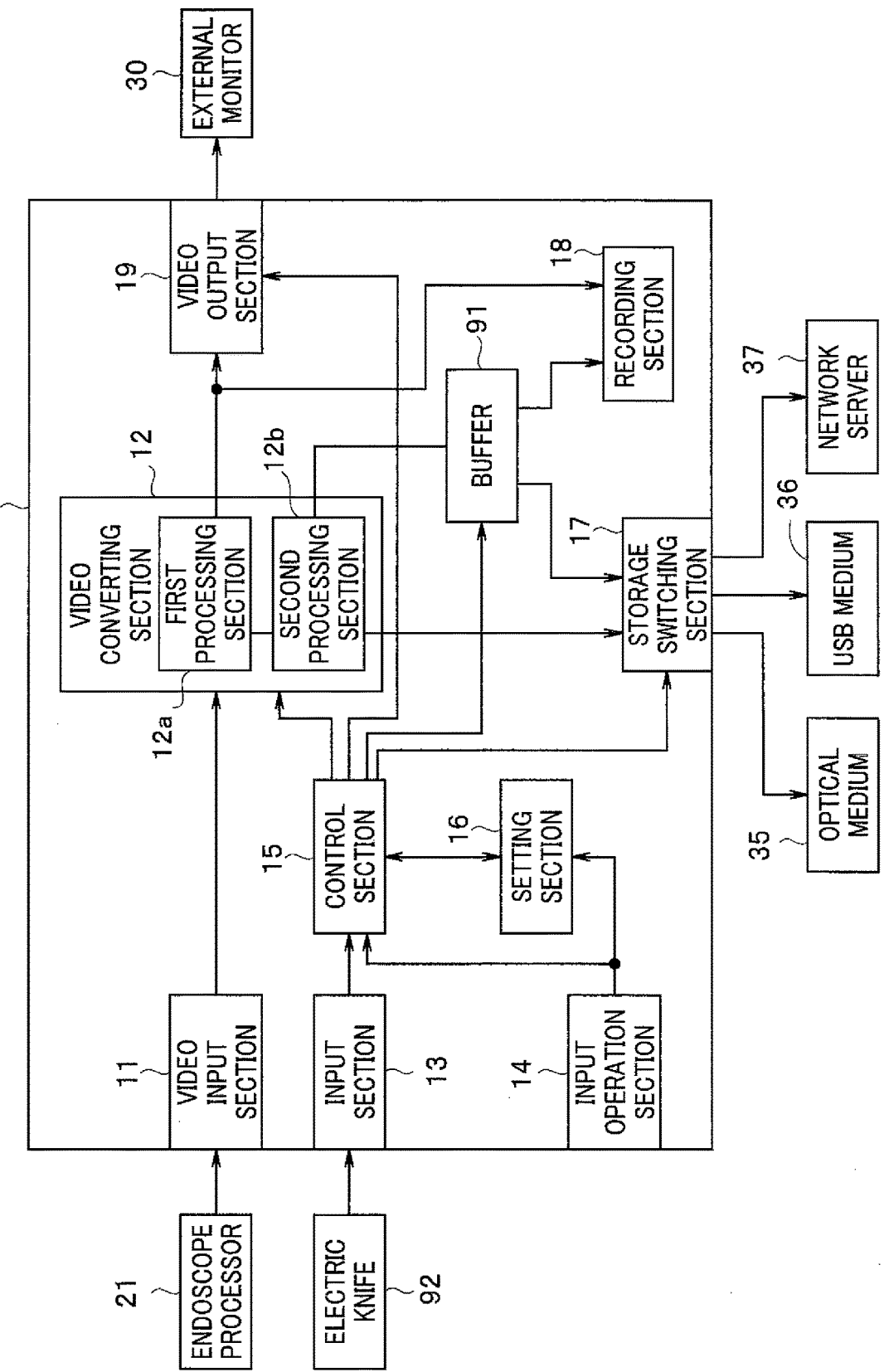
FIG. 7 is a block diagram showing a second embodiment of the present invention.

FIG. 7 is a block diagram showing a second embodiment of the present invention. In FIG. 7, components same as the components shown in FIG. 1 are denoted by the same reference numerals and signs and explanation of the components is omitted. An image recording apparatus 90 in the present embodiment is different from the image recording apparatus in the first embodiment in that a buffer 91 is adopted. In the present embodiment, an example is explained in which the input section 13 inputs an output signal of a high-frequency cauterization device (hereinafter referred to as electric knife) 92 as a switching signal.

Video signals from the second processing section 12b are supplied to the recording section 18 via the buffer 91. The buffer 91 is controlled by the control section 15 to retain the video signals from the second processing section 12b for a predetermined period and output the video signals.

In the present embodiment, when a medical image is inputted via the video input section 11, the control section 15 causes not only the first processing section 12a but also the second processing section 12b to start an operation. When an output signal of the electric knife 92 is inputted as a switching signal, the control section 15 sequentially reads out, from the buffer 91, video signals recorded in the buffer 91 a predetermined time (e.g., 5 minutes) before generation timing of the switching signal and gives the video signals to the recording section 18 and the storage switching section 17. When the output signal of the electric knife 92 is stopped, the control section 15 continues supply of the video signals from the buffer 91 to the recording section 18 and the storage switching section 17 until a predetermined time (e.g., 10 minutes) after the stop of the output signal. Thereafter, the control section 15 stops the readout from the buffer 91.

Figure 8:
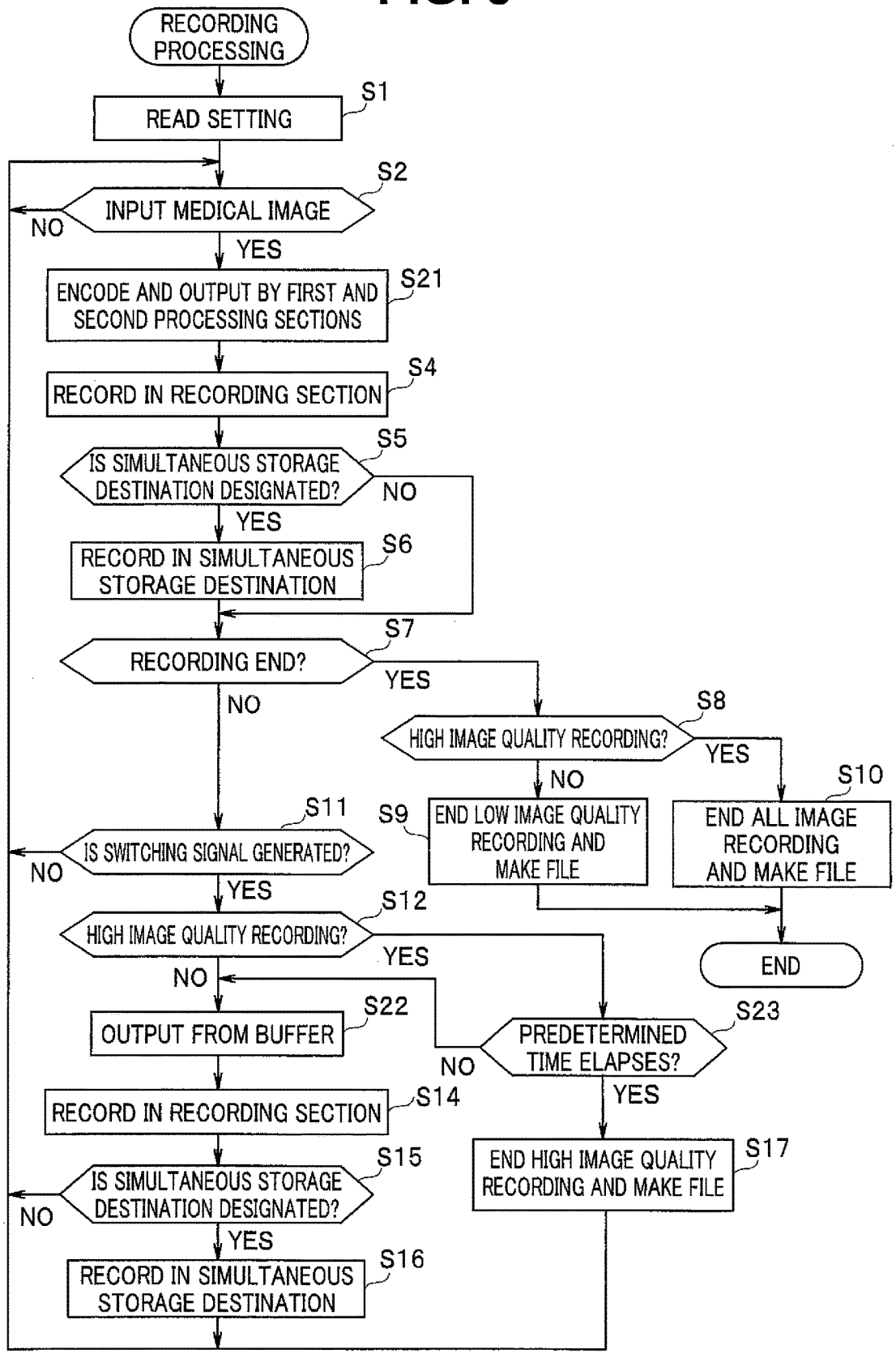
FIG. 8 is a flowchart for explaining an operation in the second embodiment.

Next, an operation in the embodiment configured as explained above is explained with reference to a flowchart of FIG. 8. In FIG. 8, procedures same as the procedures in FIG. 6 are denoted by the same signs and explanation of the procedures are omitted. A flow shown in FIG. 8 is different from the flow shown in FIG. 6 in that step S21 is adopted instead of step S3, step S22 is adopted instead of step S13, and step S23 is added.

In step S21, the control section 15 causes not only the first processing section 12a but also the second processing section 12b to operate. Consequently, a medical image is encoded to a low image quality video signal and is also encoded to a high image quality video signal. The low image quality video signal from the first processing section 12a is given to the recording section 18 and the storage switching section 17. In this way, recording of the video signals from the first processing section 12a is performed. On the other hand, the high image quality video signal from the second processing section 12b is supplied to the buffer 91 and recorded.

When an output signal from the electric knife 92 is inputted to the input section 13 as a switching signal, in step S22, the control section 15 reads out the video signals recorded in the buffer 91 and outputs the video signals to the recording section 18 and the storage switching section 17. In this case, the control section 15 sequentially reads out the video signals stored in the buffer 91 a predetermined time before generation of the switching signal and gives the video signals to the recording section 18 and the storage switching section 17. Consequently, a medical image from a predetermined time, for example, 5 minutes before a start of use of the electric knife 92 is converted into a high image quality image. Thereafter, the high image quality image is recorded by the recording section 18 and the storage switching section 17.

When the output of the electric knife 92 is stopped, the control section 15 shifts the processing from step S12 to step S23 and determines whether a predetermined time, for example, 10 minutes elapses. When the predetermined time does not elapse, the control section 15 returns the processing to step S22 and continues the readout of the video signals from the buffer 91 and the recording of the video signals. When the predetermined time elapses, in step S17, the control section 15 ends the high-quality image recording and makes a file.

In this way, in the present embodiment, an output signal of the electric knife is used as a switching signal. For example, in a medical case, a scene in which the electric knife or the like is used is an extremely important scene. By using the output signal of the electric knife as the switching signal, it is possible to automatically record, with a high image quality video signal, a state of treatment by the electric knife. By once giving a high image quality video signal from the second processing section to the buffer, causing the buffer to retain the high image quality video signal, and reading out the high image quality video signal, it is possible to record the high image quality video signal before generation of the switching signal. In the important scene in which the electric knife is used, a recording of a process to the important scene is extremely useful as recording for education. The surgeon can unintentionally record such an important scene as a high image quality image. This is excellent in convenience. Even when the output signal of the electric knife is stopped, the recording by high image quality continues for a predetermined time. Even when use and nonuse of the electric knife is frequently repeated, for example, when the electric knife is actually used, it is possible to continuously record a series of states of use of the electric knife at high image quality. It is possible to perform extremely excellent recording as recording for education.

In the present embodiment, as in the first embodiment, in one medical case, low image quality encode and recording are continuously performed by the first processing section.

Note that, in the present embodiment, the output signal of the electric knife is used as the switching signal. However, it is evident that various output signals generated in the important scene can be used as switching signals.

(Third Embodiment)

Figure 9:
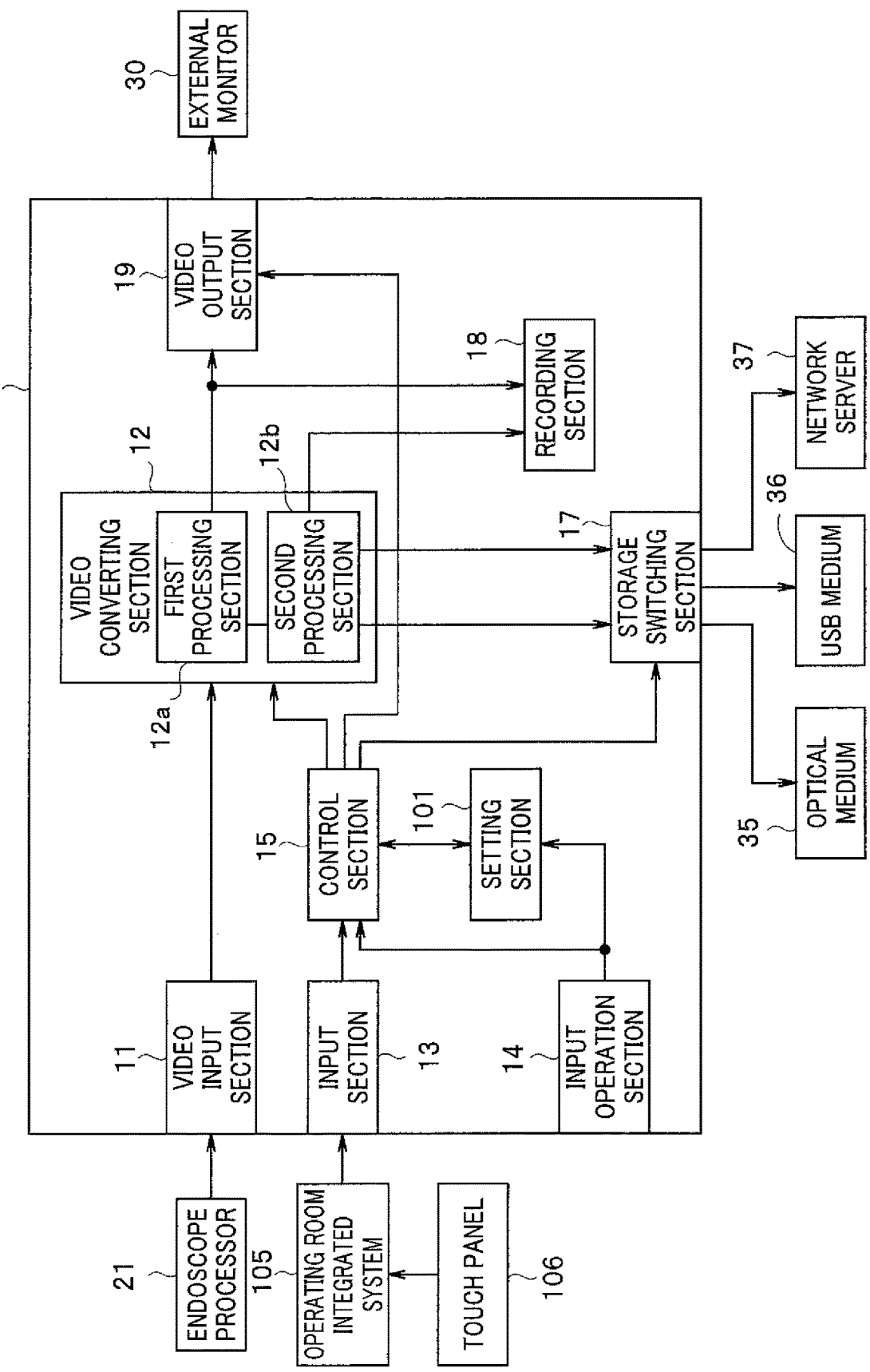
FIG. 9 is a block diagram showing a third embodiment of the present invention.

FIG. 9 is a block diagram showing a third embodiment of the present invention. In FIG. 9, components same as the components shown in FIG. 1 are denoted by the same reference numerals and signs and explanation of the components is omitted.

An image recording apparatus 100 in the present embodiment is different from the image recording apparatus in the first embodiment in that a setting section 101 is adopted instead of the setting section 16. In the present embodiment, recording control is performed using an output of an operating room integrated system 105.

A general endoscopic operation system includes an endoscope for performing observation, an ultrasound observation device, a laparoscope, an endoscope processor that processes an image signal photographed by the endoscope or the like, a light source device that supplies illumination light to an object, a monitor that displays an object image, a pneumoperitoneum device used for expanding an abdominal cavity, and a treatment device for performing a manipulation, which is an electric knife for excising or coagulating a biological tissue. The operating room integrated system 105 is a system for integrally managing these devices used for an endoscopic operation.

The operating room integrated system 105 is connected to the respective devices via, for example, an interface cable to be capable of performing bidirectional communication. In the operating room integrated system 105, a touch panel 106, on which a nurse concentratedly performs operation of medical equipment, is provided. The respective devices incorporated in the operating room integrated system 105 can be controlled by the touch panel 106.

In the operating room integrated system 105, control contents of the respective devices in each of respective scenes of a medical case are stored. The operating room integrated system 105 controls the respective devices in each of the respective scenes of the medical case. For example, for each of the respective scenes, various kinds of setting such as a light amount of the light source device and pressure setting for the pneumoperitoneum device can be automatically changed by controlling the respective devices.

The operating room integrated system 105 can select respective scenes corresponding to progress of respective manipulations such as a preparation scene, a laparoscope insertion scene, and an endoscope insertion scene and performs setting corresponding to the selected scene. For example, it is possible to perform control for, for example, switching a tissue peeling scene to an anastomosis scene or the like according to progress of an operation.

In the present embodiment, for example, a scene selection signal corresponding to scene selection is inputted to the input section 13 from the operating room integrated system 105. The input section 13 outputs the scene selection signal to the control section 15. The control section 15 can grasp, with the scene selection signal, a present scene of the operating room integrated system 105.

In the present embodiment, in the setting section 101, for each of the respective scenes set by the operating room integrated system 105, setting information concerning setting of encode processing of the first and second processing sections 12a and 12b and setting of a simultaneous storage destination is stored. The control section 15 reads out, from the setting section 101, setting information corresponding to the scene designated by the scene selection signal and controls the encode processing of the first and second processing sections 12a and 12b and the storage switching section 17. The control section 15 may cause the first processing section 12a to record information concerning the selected scene in a video signal as metadata.

Note that the respective kinds of setting of the setting section 101 may be able to be directly designated from the operating room integrated system 105 to the control section 15.

Next, an operation in the embodiment configured in this way is explained with reference to Table 1. Table 1 shows setting of the first and second processing sections 12a and 12b and the storage switching section 17 for each of the respective scenes in the operating room integrated system 105.

TABLE 1

| Scene | Image quality | | Image size | | Format | | Simultaneous storage destination | |
|---|---|---|---|---|---|---|---|---|
| | Moving image 1 | Moving image 2 | Moving image 1 | Moving image 2 | Moving image 1 | Moving image 2 | Moving image 1 | Moving image 2 |
| Preparation | Low | — | SD | — | MPEG4 | — | BD | — |
| Observation | Low | — | SD | — | MPEG4 | — | BD | — |
| Lesion part check | Low | High | SD | Full HD | MPEG4 | MPEG4 | BD | USB |
| Excision | Low | High | SD | Full HD | MPEG4 | MPEG4 | BD | USB |
| Bleeding check | Low | — | SD | — | MPEG4 | — | BD | — |
| Suture | Low | High | SD | Full HD | MPEG4 | MPEG4 | BD | USB |

In an example shown in Table 1, for example, in a preparation scene in the operating room integrated system 105, only the first processing section 12a starts an operation. In this case, low image quality is adopted as the image quality, an SD size is adopted as the image size, and MPEG-4AVC/H.264 is adopted as the format. A Blu-ray disk (BD) is adopted as the simultaneous storage destination.

In an important scene in the operating room integrated system 105, for example, in an excision scene in Table 1, not only the first processing section 12a but also the second processing section 12b starts an operation. In this case, high image quality is adopted as the image quality, a full HD size is adopted as the image size, MPEG-4AVC/H.264 is adopted as the format, and USB is adopted as the simultaneous storage destination by the second processing section 12b. In this way, in the excision scene, recording at low image quality can be performed by the first processing section 12a. Recording at high image quality can be performed by the second processing section 12b.

In table 1, encode processing in the first processing section 12a does not change. In the second processing section 12b, only one kind of encode processing is adopted. However, setting of contents of the encode processing and the simultaneous storage destination may be changed for each of the scenes.

In this way, in the present embodiment, the setting section can store a plurality of kinds of setting respectively as setting in the first processing section and setting in the second processing section. The control section selects and reads out setting information of the setting section according to a medical case scene. Consequently, it is possible to perform recording corresponding to the respective scenes. The encode processing of the first and second processing sections is controlled on the basis of the scene selection signal of the operating room integrated system. It is possible to automatically perform optimum recording according to, for example, progress of a manipulation. Since the information concerning the scenes is written in the recording data as the metadata. Therefore, it is easy to perform a search using the metadata during the search.

Note that, in the present embodiment, the encode processing of the first and second processing sections, the simultaneous storage destination, and the like may be controlled by the operating room integrated system.

(Fourth Embodiment)

Figure 10:
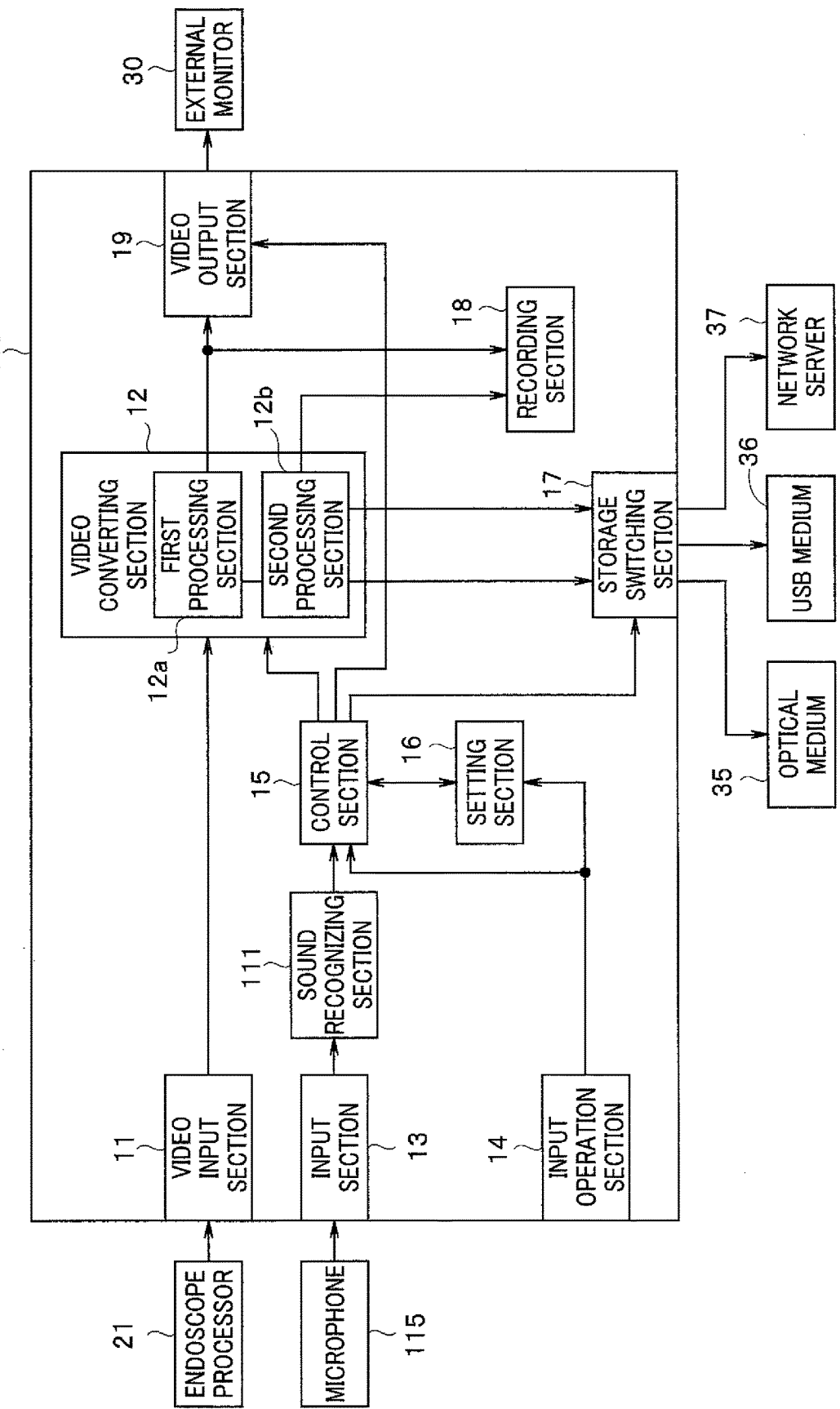
FIG. 10 is a block diagram showing a fourth embodiment of the present invention.

FIG. 10 is a block diagram showing a fourth embodiment of the present invention. In FIG. 10, components same as the components shown in FIG. 1 are denoted by the same reference numerals and signs and explanation of the components is omitted. An image recording apparatus 110 in the present embodiment is different from the image recording apparatus in the first embodiment in that a sound recognizing section 111 is added. The image recording apparatus 110 in the present embodiment is different from the image recording apparatus in the first embodiment in that recording control is performed by a sound input of a microphone 115 instead of the switching operation section 22.

A sound signal from the microphone 115 is supplied to the sound recognizing section 111 via the input section 13. The sound recognizing section 111 outputs, through sound recognition processing for an inputted sound signal, an operation signal based on sound emitted by a surgeon to the control section 15.

For example, an operation signal for instructing recording by the first processing section 12a and an operation signal for instructing recording by the second processing section 12b can be generated by the sound recognizing section 111. For example, when the surgeon utters "switch image quality" to the microphone 115, the sound recognizing section 111 outputs an operation signal for starting or ending the operation of the second processing section 12b to the control section 15. For example, when the surgeon utters "high image quality" or "setting 1" to the microphone 115, the sound recognizing section 111 can designate a type of setting information selected by the. Control section 15. For example, even when the first and second processing sections 12a and 12b and the like are controlled on the basis of a plurality of kinds of setting information as in the third embodiment, it is possible to perform selection of setting information using sound.

Note that the control section 15 may cause the first processing section 12a to record information concerning a sound recognition result in a video signal as metadata. The surgeon can directly designate setting contents of the first and second processing sections 12a and 12b using sound.

Other components and action and effects are the same as those in the first embodiment.

In this way, in the present embodiment, the surgeon can control recording using sound. Since the information concerning the scenes is written in the recording data as the metadata, it is easy to perform a search using the metadata during the search.

(Fifth Embodiment)

Figure 11:
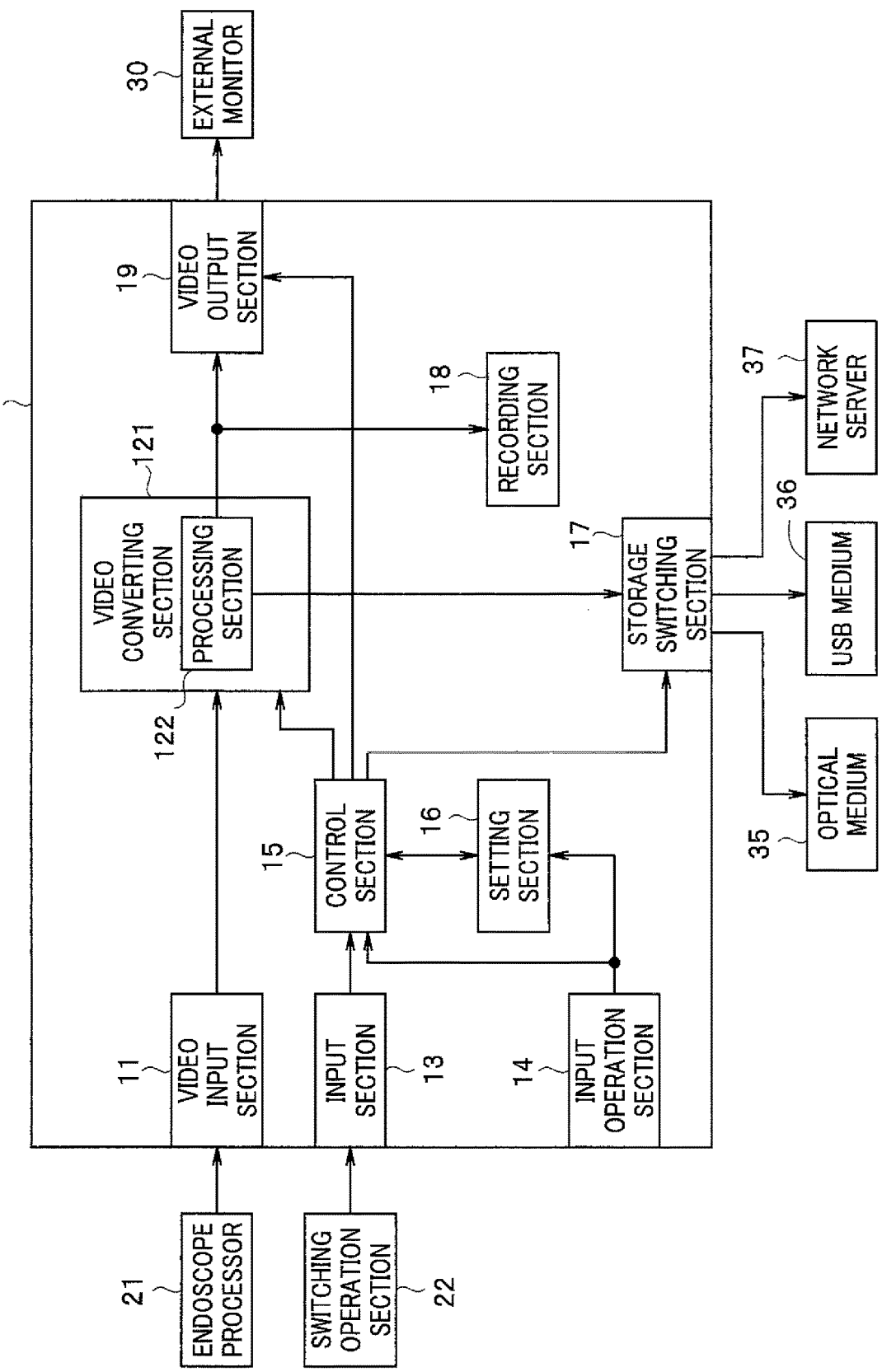
FIG. 11 is a block diagram showing a fifth embodiment of the present invention.

FIG. 11 is a block diagram showing a fifth embodiment of the present invention. In FIG. 11, components same as the components shown in FIG. 1 are denoted by the same reference numerals and signs and explanation of the components is omitted.

In the first to fourth embodiments, it is possible to simultaneously perform encode and recording at low image quality and encode and recording at high image quality by causing the first processing section 12a and the second processing section 12b to simultaneously operate. On the other hand, an image recording apparatus 120 in the present embodiment is different from the image recording apparatus in the first embodiment in that a video converting section 121 including a processing section 122 of one system is adopted and encode and recording at low image quality and encode and recording at high image quality are alternately switched.

In the present embodiment, the video converting section 121 includes only the processing section 122 of one system, encode processing of which is controlled on the basis of setting information. The setting section 16 has stored therein, for example, first setting information for low image quality and second setting information for high image quality. Every time a switching signal is inputted, the control section 15 alternately switches and reads out the first setting information and the second setting information from the setting section 16 and controls the processing section 122 and the storage switching section 17 according to the read-out setting information. Consequently, every time the switching signal is inputted, the processing section 122 and the storage switching section 17 switch encode processing and a storage destination based on the first setting information and encode processing and a storage destination based on the second setting information.

In the embodiment configured in this way, in an initial state, for example, encode processing of the processing section 122 is controlled by the control section 15 on the basis of the first setting information. In this way, a medical image is encoded and recorded as a low image quality video signal. When a switching signal is generated, the control section 15 reads out the second setting information from the setting section 16 and controls the encode processing of the processing section 122 on the basis of the second setting information. In this way, the medical image is encoded and recorded as a high image quality video signal. Thereafter, every time the switching signal is generated, the first setting information and the second setting information are alternately read out. Switching of low image quality recording and high image quality recording and setting of a storage destination are performed.

In this way, in the present embodiment, in one medical case, it is possible to switch recording at relatively low image quality for backup and recording at relatively high image quality for education. The switching can be performed by simple operation of the surgeon operating a switching operation section such as scope switches. According to the simple operation by the surgeon, it is possible to perform recording while switching image quality according to use. This is excellent in convenience.

Incidentally, in the first to fourth embodiments, the video signal generated by the first processing sections 12a and the video signal generated by the second processing sections 12b have independent time codes. A common clock may be used in the first and second processing sections 12a and 12b to embed and record, in at least one of the video signals from the first and second processing sections 12a and 12b, meta-information corresponding to the time code of the other video signal. Consequently, during reproduction of the video signal by the first processing section 12a, it is also possible to automatically start reproduction of the video signal by the second processing section 12b at timing when the high image quality recording is performed.

Figure 12:
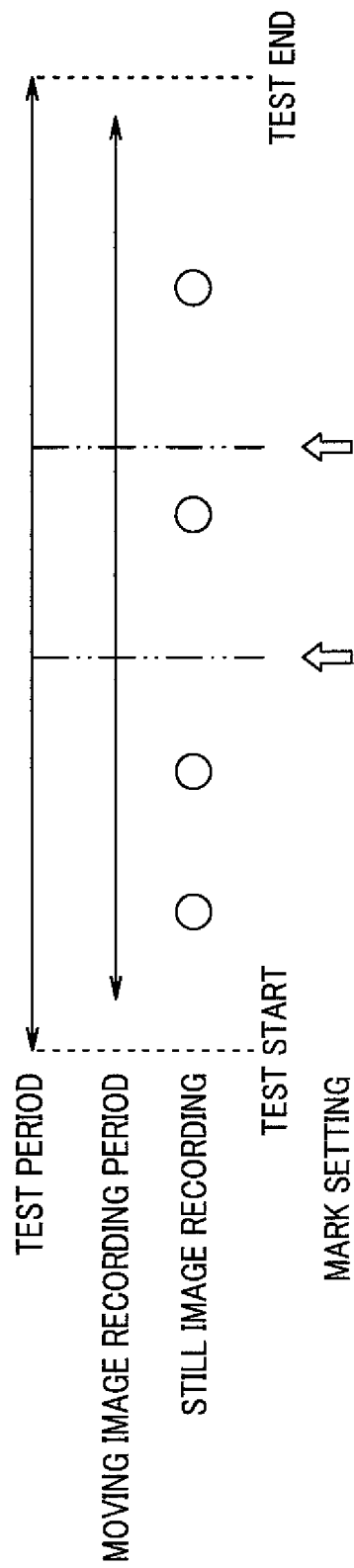
FIG. 12 is an explanatory diagram for explaining timings for embedding marks.

In the first to fourth embodiments, it is also possible to embed and record mark section information in the video signal by the first processing section 12a. FIG. 12 is an explanatory diagram for explaining embedding timing of the mark section information.

For example, the control section 15 can recognize that a start time and an end time of a mark section are designated according to operation of the scope switches or the like. The start time and the end time of the mark section may be instructed by operation of buttons or the like of a front panel of the endoscope processor 21 or may be instructed by an infrared remote controller, a touch panel, or an external keyboard. Further, a period in which the scope switches are pressed may be set as the mark section.

When the start time and the end time of the mark section are designated, the control section 15 causes the first processing section 12a to insert mark section information indicating the start and end times of the mark section into a video signal. The control section 15 can also control the video output section 19 to display a display indicating the mark section on the external monitor 30 or display the display on a display section of a main body.

In FIG. 12, with a time axis set on a lateral axis, the setting of the start and end times of the mark section is shown. As shown in FIG. 12, in a part of an entire test period, a moving image recording period for performing recording of a medical image is set. In an example shown in FIG. 12, circles indicate that still image recording is performed four times in the entire test period. Arrows in FIG. 12 indicate the start time and the end time of the mark section. When the scope switches or the like are operated at the timings of the arrows, the mark section information is inserted into the video signal. The mark section from the start time to the end time is set.

It is also possible to set the mark section using a switching signal from the switching operation section 22 that controls the operation of the second processing section 12b. That is, in this case, in the mark section, it is possible to record not only a low image quality video signal by the first processing section 12a but also a high image quality video signal by the second processing section 12b. In the mark section, it is also possible to perform recording in other simultaneous storage destinations. Further, in the mark section, it is also possible to change an image size, a format, and the like.

Since the mark section information is embedded in the video signal in this way, by adding marks to images (thumbnails) created in the mark section, it is also possible to make it easy to distinguish the images from other files. It is easy to search for an image recorded in the mark section.

When video data created in the mark section is written out, a comment may be added as metadata. Note that the comment to be added as the metadata may be set in advance or may be inputted during the setting of the mark section or after an operation ends. Consequently, it is further easier to identify the video data in the mark section.

In this way, it is possible to insert, with simple operation, the mark section information designating a desired section into a video signal recorded on a real-time basis during an operation. When a recorded image is referred to or written out, it is possible to easily identify the video data recorded in the mark section. It is possible to save labor required after the operation and improve convenience of use.

(Sixth Embodiment)

Figure 13:
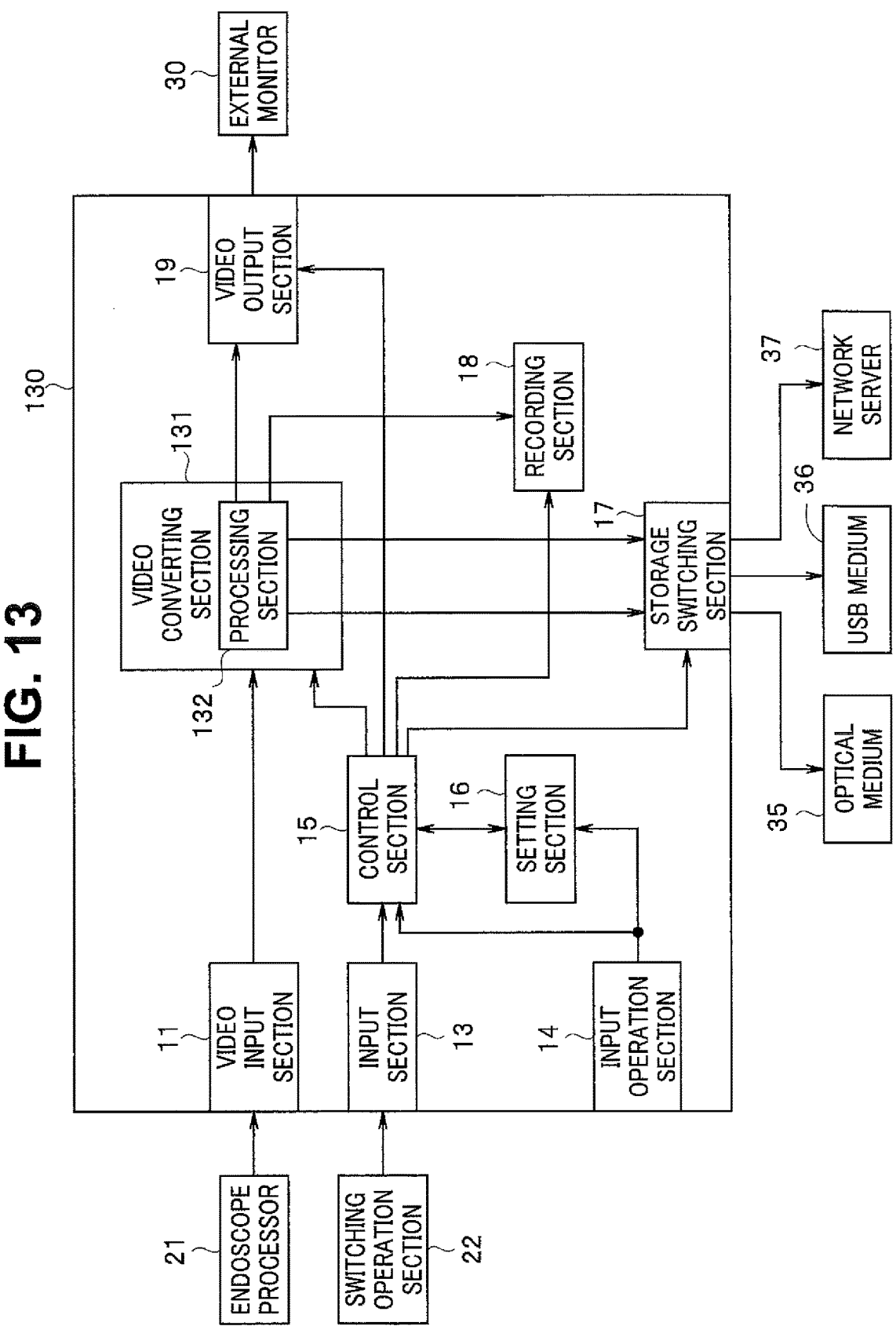
FIG. 13 is a block diagram showing a sixth embodiment of the present invention.

FIG. 13 is a block diagram showing a sixth embodiment of the present invention. In FIG. 13, components same as the components shown in FIG. 1 are denoted by the same reference numerals and signs and explanation of the components is omitted.

In the first to fourth embodiments, it is possible to simultaneously perform encode and recording at low image quality and encode and recording at high image quality by causing the first processing section 12a and the second processing section 12b to simultaneously operate. On the other hand, an image recording apparatus 130 in the present embodiment is different from the image recording apparatus in the first embodiment in that a video converting section 131 including a processing section 132 of one system is adopted and both of low image quality encode processing and high image quality encode processing are executed in a time division manner.

In the present embodiment, the video converting section 131 includes only the processing section 132 of one system, encode processing of which is controlled on the basis of setting information. In the present embodiment, the control section 15 and the setting section 16 perform processing same as the processing in the first embodiment. The video converting section 131 can select and execute, on the basis of setting information, any one encode processing of the two kinds of encode processing and can also simultaneously execute both the kinds of encode processing in a time division manner.

Figure 14:
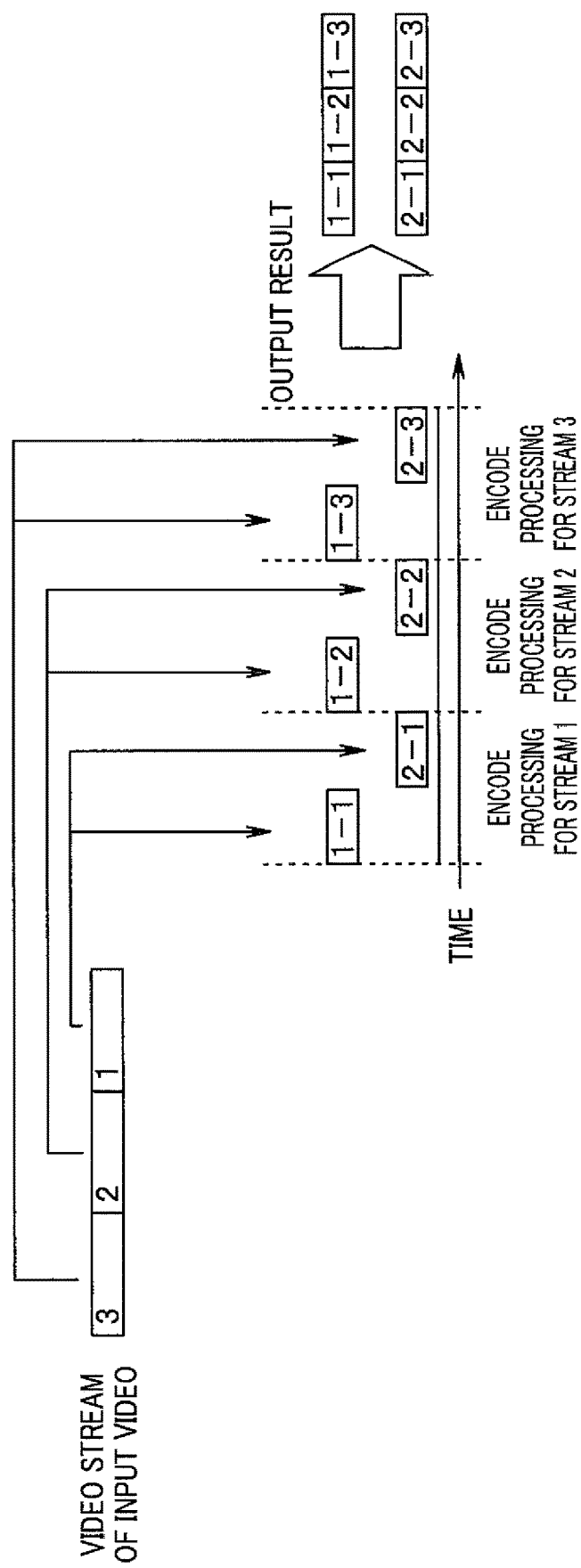
FIG. 14 is an explanatory diagram for explaining an operation in the sixth embodiment.

Next, an operation of the embodiment configured in this way is explained with reference to FIG. 14. FIG. 14 is an explanatory diagram for explaining a stream of an input video signal inputted to the video converting section 131 via the video input section 11 and encode processing and output processing for the input video signal.

In the present embodiment, as in the first embodiment, recording of a medical case or the like is performed on the basis of the setting information set in the setting section 16. For example, according to the setting information, encoding processing to an image at a relatively low bit rate, for example, an image of SD image quality is designated and encoding processing to an image at a relatively high bit rate, for example, an image of full HD image quality is designated with respect to an input video signal.

The control section 15 controls the video converting section 131 on the basis of the setting information. That is, when a medical image is given to the video converting section 131 via the video input section 11, the control section 15 controls the video converting section 131 to start encode of the medical image.

For example, it is assumed that video streams of an input video signal shown in FIG. 14 are inputted to the video converting section 131. Numbers shown in the video streams in FIG. 14 indicate order of the input of the video streams. Processing for the respective video streams is performed in time periods among broken lines shown in FIG. 14. In the present embodiment, the video converting section 131 sets, concerning each of the respective streams 1, 2, and the like, two kinds of encode systems in a time division manner and performs encode. Signs 1-1, 1-2, 1-3, and the like in FIG. 14 indicate encoding processing at SD image quality for the video streams 1, 2, 3, and the like of the input video signal. On the other hand, signs 2-1, 2-2, 2-3, and the like in FIG. 14 indicate encoding processing at HD image quality for the video streams 1, 2, 3, and the like of the input video signal.

As shown in FIG. 14, the video converting section 131 applies the two kinds of encode processing to the video streams 1, 2, 3, and the like of the input video signal in a time division manner and outputs by the respective kinds of encode processing via not-shown respective output ports. In this way, the outputs by the two kinds of encode processing for the input video signal can be obtained from the video converting section 131 via the respective output ports.

The control section 15 is capable of controlling outputs of which encode systems being outputted from the respective output ports of the video converting section 131. Consequently, for example, it is possible to give a video signal of HD image quality to the video output section 19 and give a video signal of SD image quality to the recording section 18.

Note that the video output section 19 includes a not-shown buffer and can output video streams, which are outputted in a time division manner, to the external monitor 30 as a series of video signals. The recording section 18 includes a not-shown buffer and is controlled by the control section 15 to be capable of sequentially recording inputted video signals. In this way, for example, it is possible to record a medical case at the SD image quality in the recording section 18 while observing the medical case or the like at high image quality in the external monitor 30.

In the present embodiment, it is possible to obtain effects same as the effects in the first embodiment.

(Seventh Embodiment)

Figure 15:
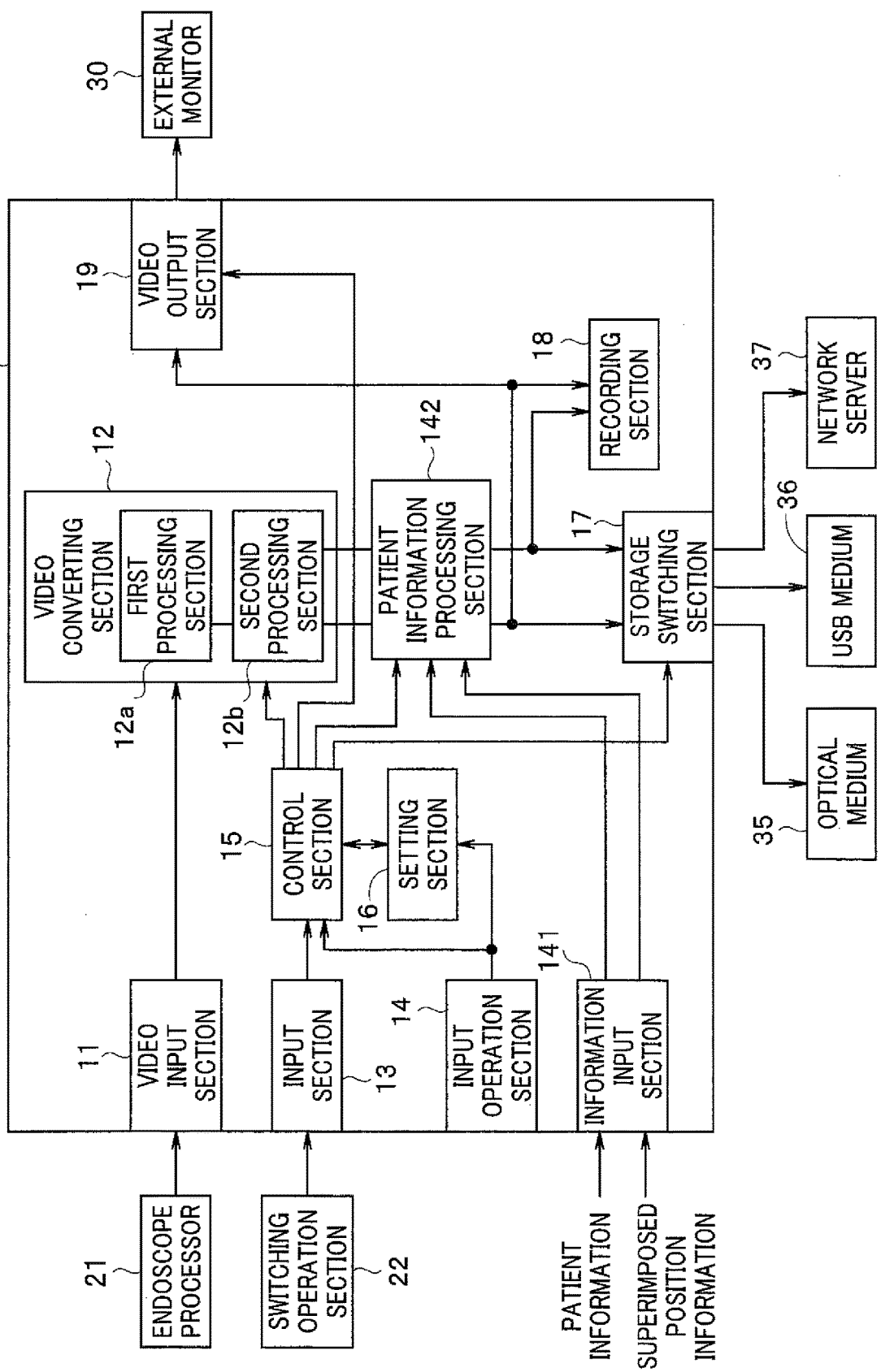
FIG. 15 is a block diagram showing a seventh embodiment of the present invention.

FIG. 15 is a block diagram showing a seventh embodiment of the present invention. In FIG. 15, components same as the components shown in FIG. 1 are denoted by the same reference numerals and signs and explanation of the components is omitted.

An image recording apparatus 140 in the present embodiment is different from the image recording apparatus 10 in the first embodiment in that an information input section 141 and a patient information processing section 142 are added.

In order to effectively utilize a medical image such as an endoscopic image for a certain patient, it is conceivable to record various kinds of information (patient information) concerning the patient in association with the medical image. For example, a medical image is sometimes adopted in which an image based on patient information such as an ID, a name, sex, and age of the patient (hereinafter referred to as patient information image) is superimposed.

In diagnosis, education, and the like performed using the medical image, the patient information image is extremely useful. For example, the endoscope processor 21 can superimpose the patient information image on the medical image. When the patient information image is superimposed on the medical image from the endoscope processor 21, the patient information image is also included in a medical image recorded in the recording section 18 in the image recording apparatus 140. However, for example, when a medical image is recorded in an external medium and disclosed, it is often preferable that patient information is not superimposed, for example, from the viewpoint of privacy protection for the patient.

Therefore, in the present embodiment, irrespective of whether the patient information image is superimposed on the medical image from the endoscope processor 21, the image recording apparatus 140 is configured to be capable of setting, according to, for example, an output destination of the medical image, whether the patient information or the patient information image is added.

Figure 16:
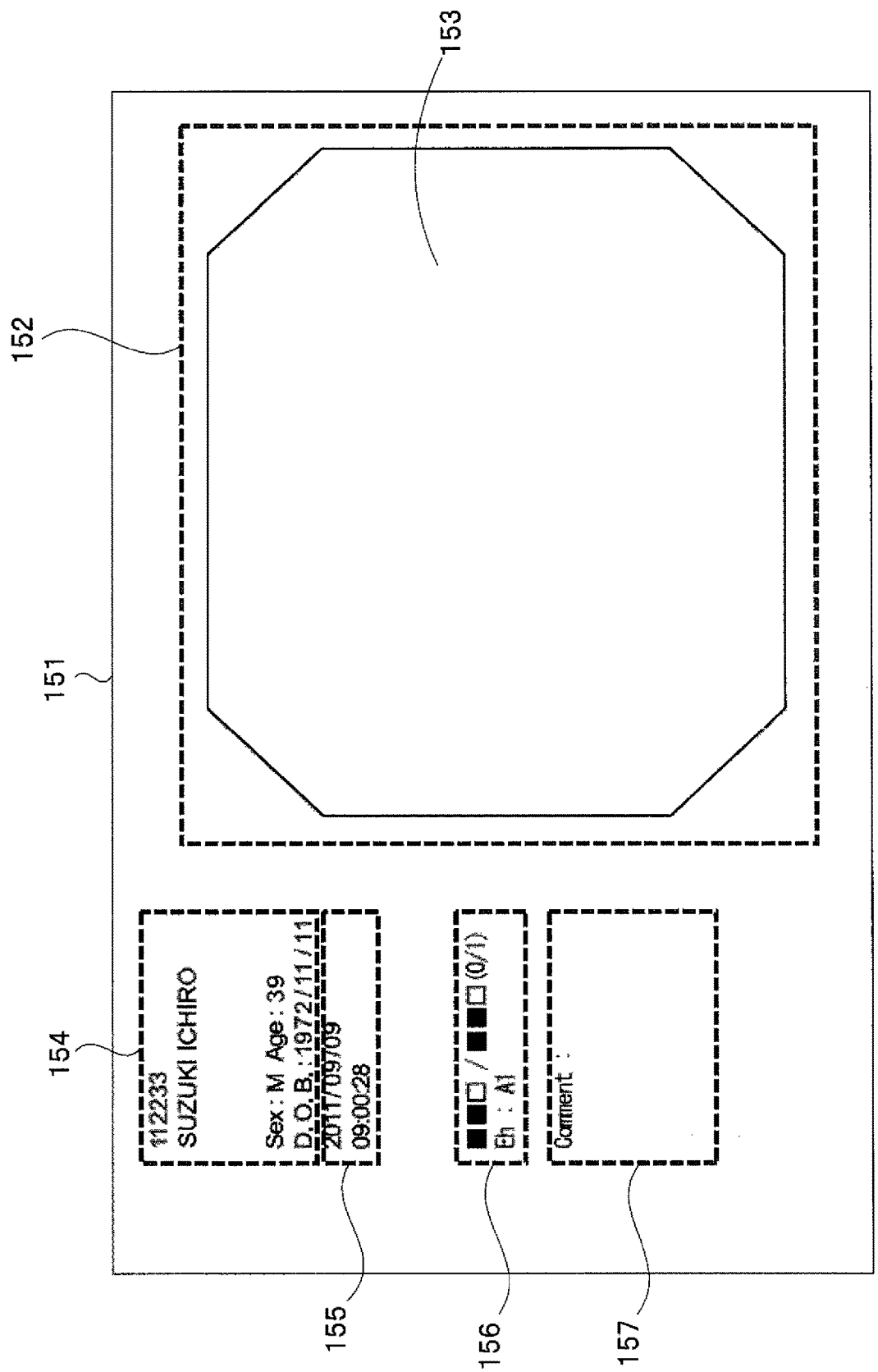
FIG. 16 is an explanatory diagram showing a medical image from an endoscope processor 21.

FIG. 16 is an explanatory diagram showing an example of a medical image from the endoscope processor 21. FIG. 16 shows an example of a medical image displayed on a display screen 151 of a not-shown display section. An endoscope screen area 152 for displaying an endoscopic image from a not-shown endoscope is provided on the display screen 151. In the endoscope screen area 152, an endoscopic image 153 is displayed (not shown in the figure). On a left side of the endoscope screen area 152, a patient information display area 154, a date and time display area 155, an apparatus information display area 156, and a comment display area 157 are provided.

The patient information display area 154 is an area for displaying a patient information image 154a. A patient information image showing, for example, a management ID, a name, sex, age, and a date of birth is displayed. In the date and time display area 155, for example, present time is displayed. In the apparatus information display area 156, for example, setting information such as a memory residual capacity and devices is displayed. In the comment display area 157, for example, an arbitrary memorandum is displayed.

In FIG. 15, the patient information image is sometime superimposed and is sometimes not superimposed on the medical image from the endoscope processor 21. When the patient information image is superimposed on the medical image, superimposing position information indicating a superimposing position on a screen of the patient information image is given to the information input section 141. Patient information is also inputted to the information input section 141. Note that, as the information input section 141, for example, an interface based on an RS-232C standard can be adopted.

The information input section 141 outputs the inputted patient information and superimposing position information to the patient information processing section 142. The patient information processing section 142 is controlled by the control section 15 to perform, according to setting information of the setting section 16, addition processing for the patient information and deletion processing for the patient information image.

When the patient information image is superimposed on the medical image from the video converting section 12, the patient information processing section 142 can delete the patient information image from the medical image by superimposing a predetermined mask image in the superimposing position of the patient information image on the basis of the superimposing position information. The patient information processing section 142 can add the inputted patient information to the medical image as meta-information.

In this way, the medical image including the patient information image, the medical image to which the patient information is added as the meta-information, the medical image to which the patient information is not added, the medical image from which the patient information image is deleted, and the like are outputted from the patient information processing section 142 to the storage switching section 17, the recording section 18, and the video output section 19 on the basis of the setting information.

Next, an operation of the embodiment configured in this way is explained with reference to explanatory diagrams of FIG. 17 to FIG. 20.

It is assumed that the patient information image is not included in the medical image inputted to the video input section 11. In this case, the patient information image is not included in medical images from the first and second processing sections 12a and 12b of the video converting section 12. The patient information processing section 142 is controlled by the control section 15 on the basis of the setting information of the setting section 16 to output the medical images from the first and second processing sections 12a and 12b with the patient information added thereto or directly output the medical images without adding the patient information thereto.

For example, it is assumed that setting information for not adding the patient information to the medical image outputted by the first processing section 12a and adding the patient information to the medical image outputted by the second processing section 12b is stored in the setting section 16. In this case, the patient information processing section 142 is controlled by the control section 15 to directly output a low image quality medical image from the first processing section 12a without adding the patient information thereto. On the other hand, the patient information processing section 142 outputs a high image quality medical image from the second processing section 12b after adding the patient information as meta-information.

In this way, for example, the medical image recorded in the recording section 18 is recorded with the patient information added as the meta-information. The medical image recorded in the external medium from the storage switching section 17 is recorded without the patient information added thereto.

Figure 17:
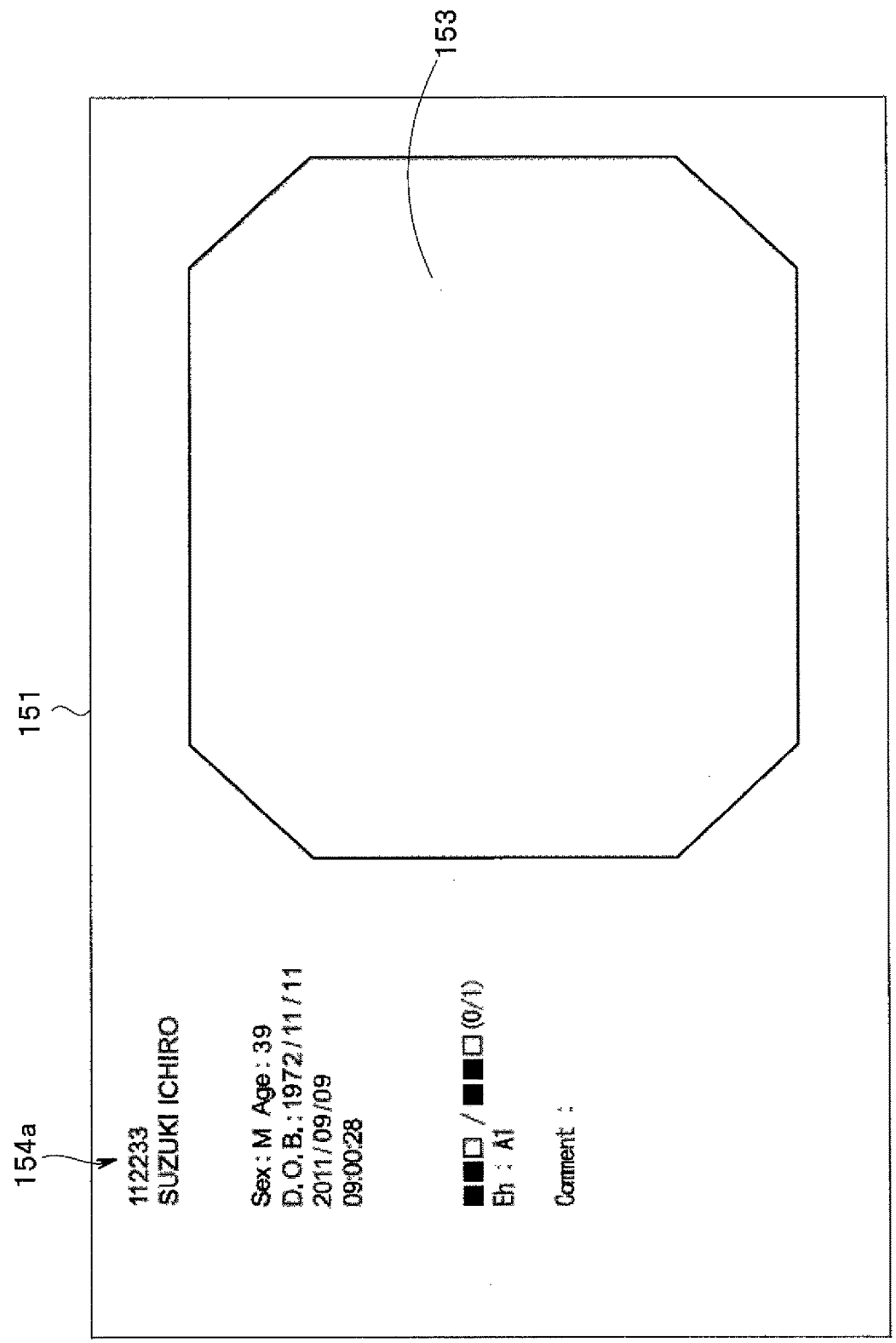
FIG. 17 is an explanatory diagram for explaining the seventh embodiment.

Next, it is assumed that the patient information image is included in the medical image inputted to the video input section 11. FIG. 17 shows an example of such a medical image and shows a state in which the patient information image 154a is displayed in the medical image. In the example shown in FIG. 17, the patient information image 154a indicates that a patient of the endoscopic image 153 is a patient whose management ID is 112233, name is SUZUKI ICHIRO, sex is male, age is 39, and date of birth is Nov. 11, 1972.

In this case, the patient information image is also kept included in the medical images from the first and second processing sections 12a and 12b of the video converting section 12. The patient information processing section 142 generates a mask image corresponding to the patient information display area 154 on the basis of the superimposing position information. The patient information processing section 142 is controlled by the control section 15 on the basis of the setting information of the setting section 16 to determine whether a mask image is superimposed on the patient information display area 154 in the medical images from the first and second processing sections 12a and 12b. The patient information processing section 142 superimposes the mask image on the patient information display area 154, whereby the patient information image is deleted.

For example, it is assumed that setting information for not superimposing the mask image on the medical image outputted by the first processing section 12a and superimposing the mask image on the medical image outputted by the second processing section 12b is stored in the setting section 16. In this case, the patient information processing section 142 is controlled by the control section 15 to directly output the medical image from the first processing section 12a without superimposing the mask image. On the other hand, the patient information processing section 142 outputs the medical image from the second processing section 12b after superimposing the mask image. That is, the patient information image 154a is kept included in the medical image from the first processing section 12a. The patient information image 154a is removed from the medical image from the second processing section 12b.

Figure 18:
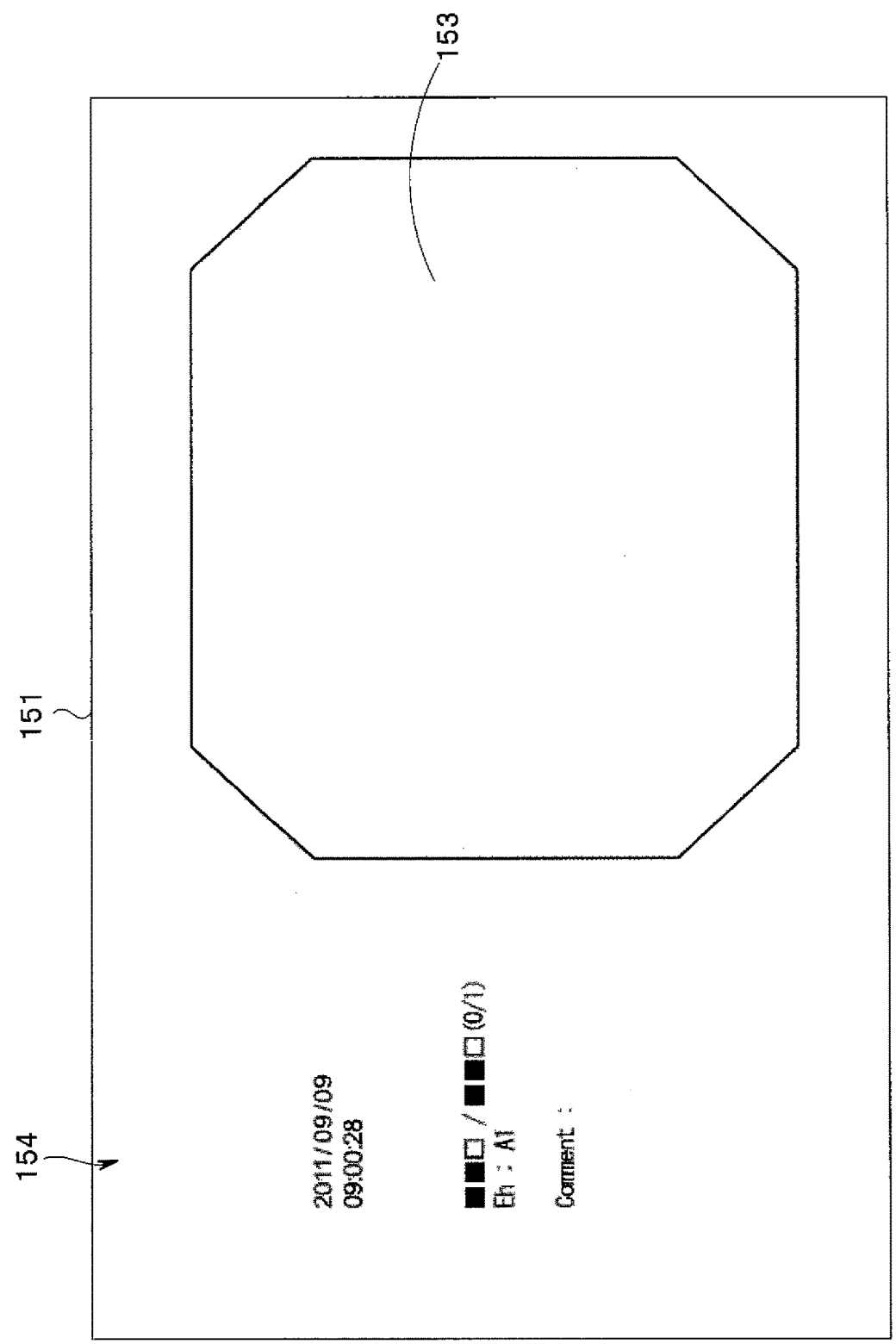
FIG. 18 is an explanatory diagram for explaining the seventh embodiment.

FIG. 18 shows a state in which the mask image is superimposed on the patient information display area 154a in the medical image shown in FIG. 17. The patient information image 154a in the medical image is covered by the mask image to be hidden. Note that in an example shown in FIG. 18, since the mask image has a color same as a color of a base of the medical image, it is unclear whether the mask image is superimposed. However, a mask image having a color different from the color of the base may be superimposed.

In this way, for example, concerning the medical image recorded in the recording section 18, the medical image in which the patient information image remains can be recorded. Concerning the medical image recorded in the external medium from the storage switching section 17, the medical image from which the patient information image is removed can be recorded.

Figure 19:
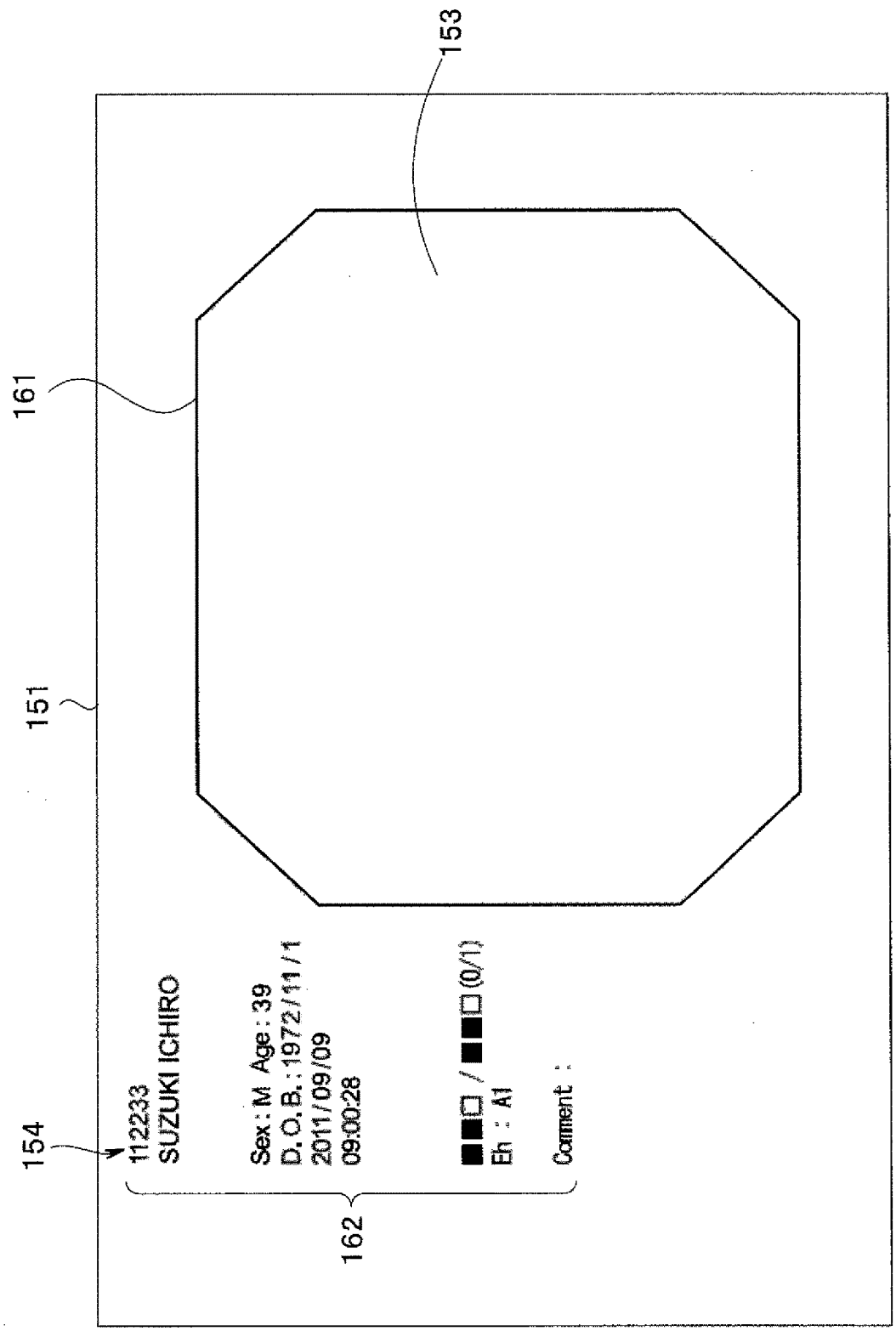
FIG. 19 is an explanatory diagram for explaining the seventh embodiment.

Note that there are various display forms of the medical image. A position in a screen of the patient information display area is different for each of the display forms. FIG. 19 shows an example in which an endoscopic image screen area 161 and a display area 162 for various kinds of information are closer to a screen center. For example, the endoscope processor 21 side sometimes has setting for changing an output image according to whether a display screen of a display section has an aspect ratio of 16:9 or an aspect ratio of 5:4. Compared with setting of the aspect ratio of 16:9, in the case of setting of 5:4, the endoscopic image screen area 161 and the display area 162 for various kinds of information are displayed in a state in which the areas are closer to the screen center.

Figure 20:
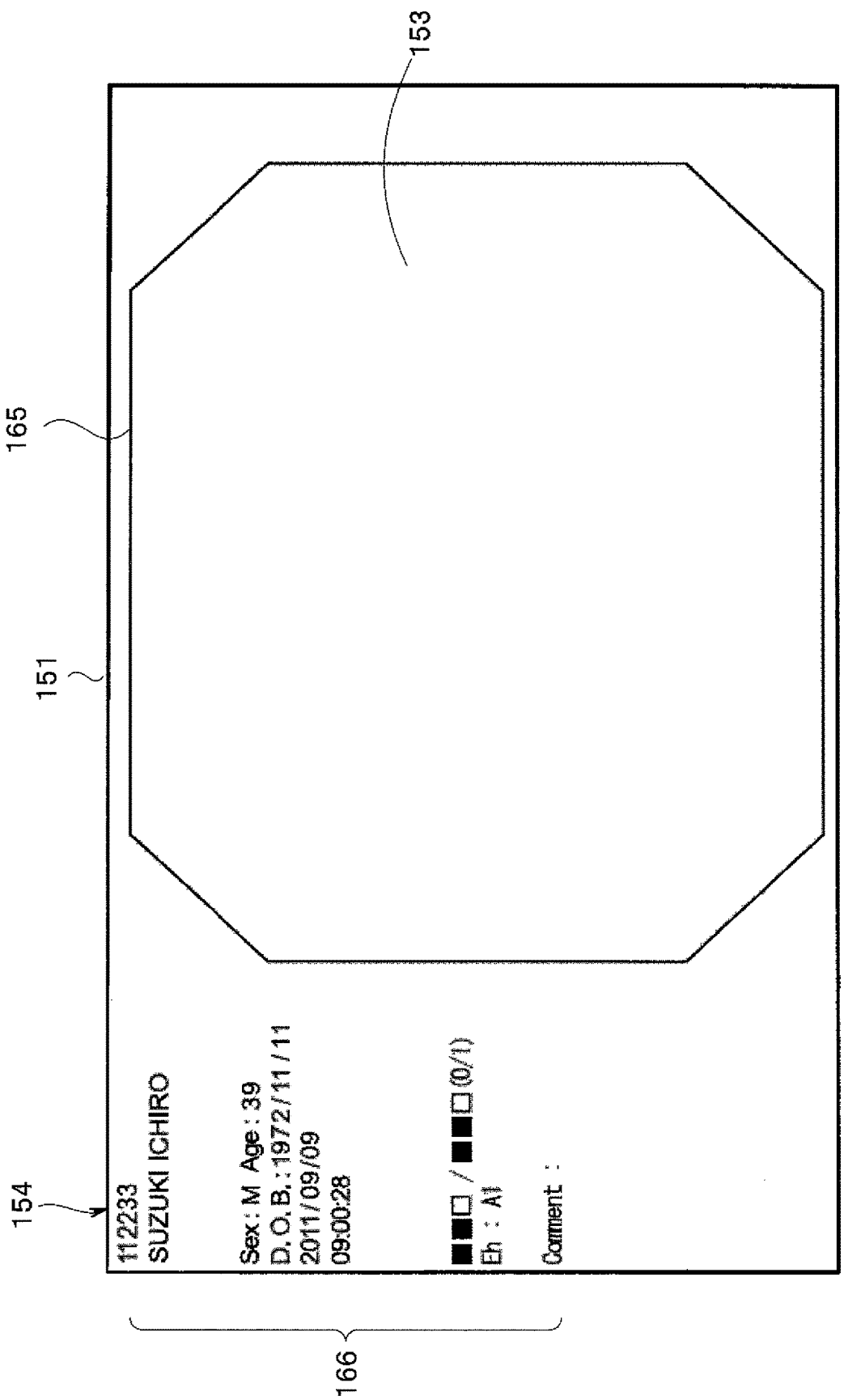
FIG. 20 is an explanatory diagram for explaining the seventh embodiment.

FIG. 20 is an example in which an entire endoscopic image screen area 165 and an entire display area 166 for various kinds of information are expanded. In the example shown in FIG. 20, the endoscopic image screen area 165 and the display area 166 for various kinds of information are expanded over a substantially entire area of the display screen 151 and displayed.

In the present embodiment, even when the patient information display area in the medical image changes, by using the superimposing position information indicating the patient information display area, the patient information processing section 142 is capable of surely deleting the patient information image. Note that, irrespective of whether the patient information image is included in the medical image, the patient information processing section 142 is capable of creating, on the basis of the setting information, the medical image to which the patient information is added as the meta-information.

In this way, in the present embodiment, on the basis of the setting information, it is possible to output the medical images from the first and second processing sections in any form, that is, output the medical images with the patient information image kept added thereto, output the medical images with the patient information image deleted therefrom, output the medical images without adding the patient information thereto, and output the medical images with the patient information added thereto. Consequently, for example, it is possible to record the medical image to which the patient image is added in recording in a built-in recording section and record the medical image from which the patient information image is removed in recording in the external medium. This is extremely useful in terms of privacy protection.

(Eighth Embodiment)

Figure 21:
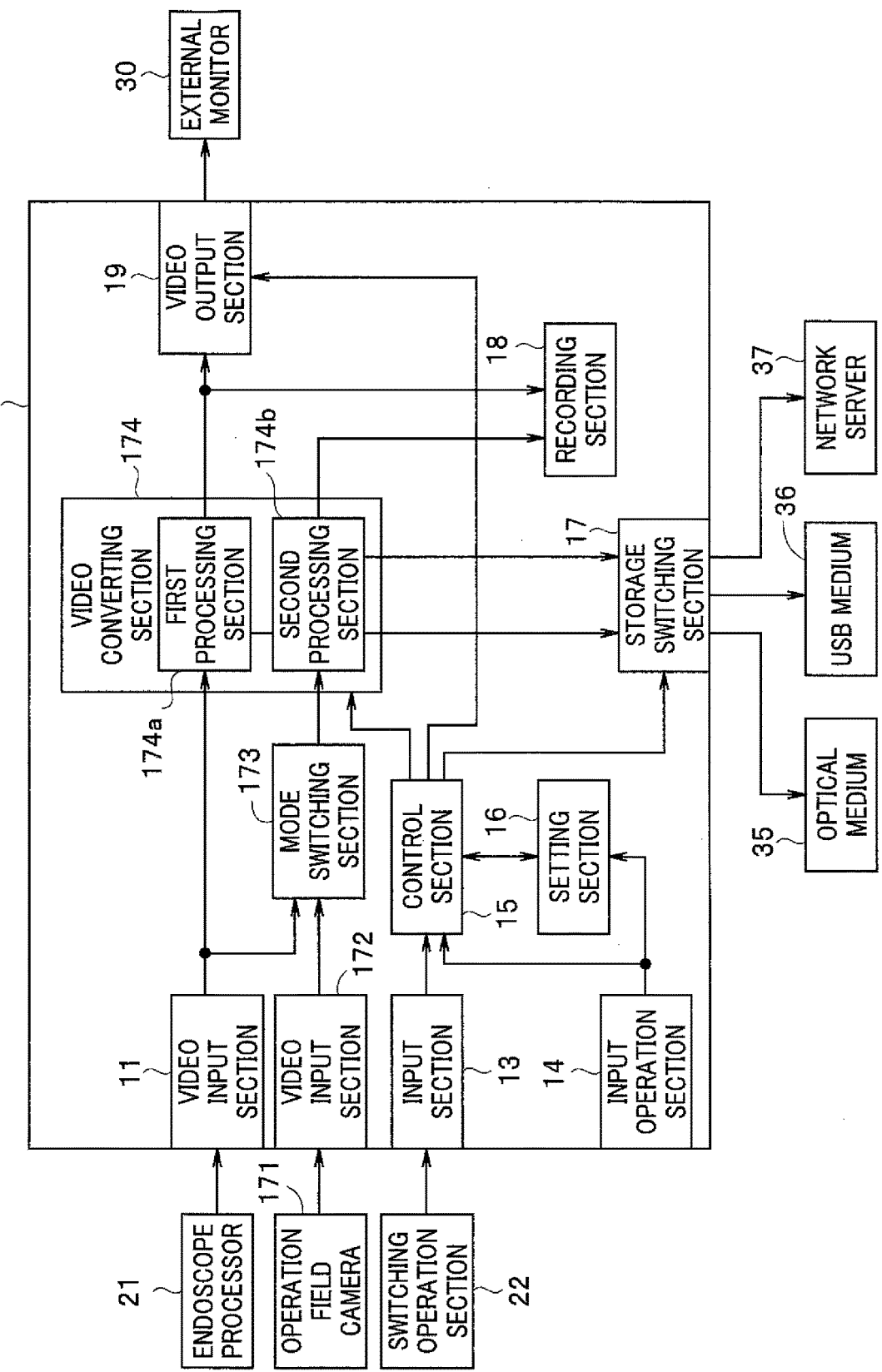
FIG. 21 is a block diagram showing an eighth embodiment of the present invention.

FIG. 21 is a block diagram showing an eighth embodiment of the present invention. In FIG. 21, components same as the components shown in FIG. 1 are denoted by the same reference numerals and signs and explanation of the components is omitted. In the first embodiment, the first and second processing sections 12a and 12b are capable of adopting various encode systems on the basis of the setting information. On the other hand, an image recording apparatus 170 in the present embodiment includes a video converting section 174 including a first processing section 174a and a second processing section 174b, an encode system of which is fixed. The first processing section 174a applies predetermined encode processing to a medical image from the endoscope processor 21 inputted via the video input section 11. For example, the first processing section 174a encodes and outputs the medical image such that a high image quality encode output is obtained. The second processing section 174b applies predetermined encode processing to a medical image from a mode switching section 173. For example, the second processing section 174b encodes and outputs the medical image such that a low image quality encode output is obtained.

Conventionally, like the first and second processing sections 174a and 174b, recording devices that individually process images from two cameras are used. The present embodiment can be configured using such devices. In the present embodiment, the mode switching section 173 can select an output of video input sections 11 and 172 and output the output to the second processing section 174b. The mode switching section 173 selects an output of the video input section 172, whereby a medical image from an operation field camera 171 is supplied to the second processing section 174b. The mode switching section 173 selects an output of the video input section 11, whereby a medical image from the endoscope processor 21 is supplied to the second processing section 174b.

Next, an operation in the embodiment configured in this way is explained.

When display, recording, and the like of the medical images from the endoscope processor 21 and the operation field camera 171 are performed, the mode switching section 173 selects an output of the video input section 172. In this case, the medical image from the endoscope processor 21 is supplied to the first processing section 174a. The medical image from the operation field camera 171 is supplied to the second processing section 174b. In this way, the medical image from the endoscope processor 21 and the medical image from the operation field camera 171 are respectively encoded and outputted by the first processing section 174a and the second processing section 174b.

On the other hand, it is assumed that display, recording, and the like are applied only to the medical image from the endoscope processor 21. In this case, the mode switching section 173 selects the output of the video input section 11. In this case, the medical image from the endoscope processor 21 is directly supplied to the first processing section 174a, supplied to the second processing section 174b via the mode switching section 173, and encoded by both of the first processing section 174a and the second processing section 174b.

For example, it is assumed that the first processing section 174a performs high image quality encode processing and the second processing section 174b performs low image quality encode processing. In this case, a medical image of an endoscope encoded at high image quality is outputted from the first processing section 174a. A medical image of the endoscope encoded at low image quality is outputted from the second processing section 174b.

Other action is the same as the action in the first embodiment.

In this way, in the present embodiment, the mode switching section that switches two inputs and supplies the inputs to the first and second processing sections is provided. Therefore, a medical image of one of the two inputs can be subjected to the encode processing of the two systems by the first and second processing sections. For example, it is possible to simultaneously obtain two kinds of encode results such as a high image quality encode output and a low image quality encode output.

Note that the present invention is not limited to the respective embodiments per se. At an implementation stage, the present invention can be embodied by modifying the constituent elements without departing from the spirit of the present invention. Various inventions can be formed according to appropriate combinations of the plurality of constituent elements disclosed in the respective embodiments. For example, several constituent elements of all the constituent elements disclosed in the embodiments may be deleted. Further, the constituent elements disclosed in the different embodiments may be combined as appropriate.

What is claimed is:

1. An image recording apparatus comprising:
   a first processing section that encodes an inputted medical image based on setting information including encode processing information and outputs a first encode result, the setting information being set for each medical case scene of a plurality of medical case scenes;
   a second processing section that encodes the inputted medical image based on the setting information including the encode processing information and outputs a second encode result;
   a setting section that stores the setting information to designate an encode method for each of the first processing section and the second processing section, and storage destination information indicating (i) a recording destination of the first encode result and the second encode result and (ii) an image quality associated with each of the first encode result and the second encode result; and
   a control section configured to:
      receive a scene selection signal corresponding to a selection of one of the plurality of medical case scenes that respectively correspond to different states of progresses of medical treatments,
      upon receiving the scene selection signal, read and determine the setting information corresponding to the selected one medical case scene of the plurality of medical case scenes in the scene selection signal,
      based on storage destination information included in the read setting information, control the first processing section and the second processing section to encode and output at least one of the first encode result and the second encode result, the control causing: (i) the first processing section to always encode and output the first encode result, and (ii) whether the second processing section encodes and outputs the second encode result based on the encoding method and the image quality of the read setting information, and
      automatically determine a recording destination of the output at least one of the first encode result and the second encode result based on the storage destination information corresponding to the scene selection signal, wherein
      the setting information is stored in a memory different from recording destinations of the first encode result and the second encode result.

2. The image recording apparatus according to claim 1, further comprising:
   a buffer configured to store the second encode result for a predetermined period of time and output the second encode result, wherein
   the control section is configured to cause the buffer to output the second encode result according to generation of the scene selection signal.

3. The image recording apparatus according to claim 1, wherein the setting information includes at least one kind of information among image quality, an image size, and a format.

4. The image recording apparatus according to claim 3, wherein the setting information includes information concerning the recording destination of the first and second encode results.

5. The image recording apparatus according to claim 1, wherein the setting information includes information concerning the recording destination of the first and second encode results.

6. The image recording apparatus according to claim 1, wherein
   the first processing section outputs the first encode result at a first image quality on the basis of the setting information, and
   the second processing section outputs the second encode result at a second image quality different from the first image quality on the basis of the setting information.

7. The image recording apparatus according to claim 1, further comprising:
   a processing section of one system configured to select and execute one of two kinds of encode processings based on respective pieces of the setting information corresponding to the two kinds of encode processings, and configured to execute both of the encode processings in a time division manner.

8. The image recording apparatus according to claim 1, further comprising:
   a patient information processing section that, on the basis of the setting information, outputs the first and second encode results with patient information added thereto or directly outputs the first and second encode results.

9. The image recording apparatus according to claim 8, wherein
   when a patient information image is superimposed on the medical image, the patient information processing section receives superimposing position information of the patient information image and generates a mask image that removes the patient information image, and based on the setting information, the patient information processing section outputs the first and second encode results with the mask image superimposed thereon or directly outputs the first and second encode results.

10. An image recording apparatus comprising:
    a memory storing a plurality of pieces of setting information in association with a plurality of medical case scenes, the setting information including: (i) encode processing information to designate an encode method for each of the first processing section and the second processing section, and (ii) storage destination information indicating (1) a recording destination of a first encode result and a second encode result and (2) an image quality associated with each of the first encode result and the second encode result; and
    a processor operatively coupled to the memory, the processor being programmed to:
       receive an inputted medical image;
       encode the inputted medical image based on a first encode processing included in a first piece of the setting information stored in the memory to produce the first encode result;

encode the inputted medical image based on a second encode processing in a second piece of the setting information stored in the memory to produce the second encode result;

receive a scene selection signal selecting one of a plurality of medical case scenes that respectively correspond to different states of progresses of medical treatments;

upon receiving the scene selection signal, read and determine the setting information corresponding to the selected one medical case scene of the plurality of medical case scenes in the scene selection signal;

based on the storage destination information included in the read setting information:
   always output the first encode result, and
   only output the second encode result based on the encoding method and the image quality of the read setting information; and automatically determine a recording destination of the output first and second encode results based on the storage destination information corresponding to the determined setting information, wherein the memory storing the setting information is different than a memory of recording destinations of the first encode result and the second encode result.

11. The image recording apparatus according to claim 10, further comprising:
   a buffer storing the second encode result for a predetermined period of time and outputting the second encode result, wherein
   the processor is configured to cause the buffer to output the second encode result in response to the received scene selection signal.

12. The image recording apparatus according to claim 10, wherein the plurality of pieces of setting information includes at least image quality, an image size, and a format.

13. The image recording apparatus according to claim 12, wherein the setting information includes information concerning the recording destination of the first and second encode results.

14. The image recording apparatus according to claim 10, wherein the setting information includes information concerning the recording destination of the first and second encode results.

15. The image recording apparatus according to claim 10, wherein the processor is further programmed to:
   output the first encode result at a first image quality on the basis of the setting information, and
   output the second encode result at a second image quality different from the first image quality on the basis of the setting information.

16. The image recording apparatus according to claim 10, wherein the processor is further programmed to:
   select and execute one of the first and second encode processings on the basis of respective pieces of the setting information corresponding to the different encode processes, and
   execute both of the first and second encode processings in a time division manner.

17. The image recording apparatus according to claim 10, wherein the processor is further programmed to:
   on the basis of the setting information, output: (A) the first and second encode results with patient information, or (B) the first and second encode results without patient information.

18. The image recording apparatus according to claim 17, wherein when a patient information image is superimposed on the medical image, the processor is further programmed to:
   receive superimposing position information of the patient information image,
   generate a mask image that removes the patient information image, and
   on the basis of the setting information, output: (A) the first and second encode results with the mask image superimposed thereon, or (B) the first and second encode results without the mask image.

19. The image recording apparatus according to claim 1, wherein the medical case scene includes at least:
   one of a scene corresponding to movement or position of respective manipulations of a tool or biological tissue, or
   one of a scene corresponding to progress or status of a medical operation or procedure.

* * * * *